(12) United States Patent
Kiniwa et al.

(10) Patent No.: US 11,736,784 B2
(45) Date of Patent: Aug. 22, 2023

(54) THREE-PLATE CAMERA AND FOUR-PLATE CAMERA

(71) Applicant: PANASONIC I-PRO SENSING SOLUTIONS CO., LTD., Fukuoka (JP)

(72) Inventors: Yuji Kiniwa, Fukuoka (JP); Yota Hashimoto, Fukuoka (JP); Yuuichi Takenaga, Fukuoka (JP)

(73) Assignee: I-PRO CO., LTD., Tokyo (JP)

( * ) Notice: Subject to any disclaimer, the term of this patent is extended or adjusted under 35 U.S.C. 154(b) by 0 days.

(21) Appl. No.: 17/232,779

(22) Filed: Apr. 16, 2021

(65) Prior Publication Data

US 2021/0329153 A1    Oct. 21, 2021

(30) Foreign Application Priority Data

Apr. 17, 2020   (JP) ................................ 2020-074282

(51) Int. Cl.
*H04N 5/00*   (2011.01)
*G02B 27/10*  (2006.01)
(Continued)

(52) U.S. Cl.
CPC ........... *H04N 23/45* (2023.01); *H04N 23/951* (2023.01); *A61B 90/361* (2016.02); *A61B 2090/3941* (2016.02)

(58) Field of Classification Search
CPC .............. H04N 5/2258; H04N 5/23232; A61B 90/361; A61B 2090/3941
See application file for complete search history.

(56) References Cited

U.S. PATENT DOCUMENTS

| 7,242,478 B1 * | 7/2007 | Dombrowski | ............ | G01J 3/02 356/419 |
| 11,113,802 B1 * | 9/2021 | Sun | .......................... | G06T 5/50 |

(Continued)

FOREIGN PATENT DOCUMENTS

| JP | 2005-176940 | 7/2005 |
| JP | 2009-290694 | 12/2009 |

(Continued)

OTHER PUBLICATIONS

Galo et al. "Registration analysis and inner calibration of a three CCD multispectral frame camera", 2006.*

(Continued)

*Primary Examiner* — James T Boylan
(74) *Attorney, Agent, or Firm* — Greenblum & Bernstein, P.L.C.

(57) ABSTRACT

A three-plate camera includes an IR prism that causes an IR image sensor to receive incident IR light of light from an observation part, a visible prism that causes a visible image sensor to receive incident visible light of light from the observation part, a specific prism that causes a specific image sensor to receive incident light of a specific wavelength band of light from the observation part, and a video signal processing unit that generates an IR video signal, a visible video signal, and a specific video signal of the observation part based on respective imaging outputs of the IR image sensor, the visible image sensor, and the specific image sensor, combines the IR video signal, the visible video signal, and the specific video signal, and outputs a combined video signal to a monitor.

13 Claims, 22 Drawing Sheets

(51) Int. Cl.
*H04N 23/45* (2023.01)
*H04N 23/951* (2023.01)
*A61B 90/00* (2016.01)

(56) References Cited

U.S. PATENT DOCUMENTS

| | | | | |
|---|---|---|---|---|
| 2002/0051073 | A1* | 5/2002 | Paavola | H04N 9/097 |
| | | | | 348/373 |
| 2004/0130649 | A1* | 7/2004 | Lee | H04N 5/272 |
| | | | | 348/E5.045 |
| 2007/0242900 | A1* | 10/2007 | Chen | H04N 5/2355 |
| | | | | 382/294 |
| 2007/0279514 | A1* | 12/2007 | Mitsumine | H04N 5/2224 |
| | | | | 348/336 |
| 2010/0225783 | A1* | 9/2010 | Wagner | H04N 5/2356 |
| | | | | 348/229.1 |
| 2013/0229544 | A1 | 9/2013 | Bando | |
| 2016/0338593 | A1 | 11/2016 | Ikehara | |
| 2017/0034499 | A1* | 2/2017 | Doron | H04N 13/25 |
| 2017/0219834 | A1 | 8/2017 | Horiguchi et al. | |
| 2019/0170647 | A1 | 6/2019 | Ikenaga et al. | |
| 2019/0361252 | A1* | 11/2019 | Nagae | G02B 21/0012 |
| 2020/0046225 | A1* | 2/2020 | Kamat | A61B 1/0646 |
| 2022/0120689 | A1 | 4/2022 | Ikenaga et al. | |

FOREIGN PATENT DOCUMENTS

| | | |
|---|---|---|
| JP | 2013-183353 | 9/2013 |
| JP | 2016-075825 | 5/2016 |
| JP | 2016-214507 | 12/2016 |
| JP | 2018-027272 | 2/2018 |
| JP | 2018-175762 | 11/2018 |

OTHER PUBLICATIONS

DuncanTech MS2100/MS2150/MS3100 User Manual for Digital Multispectral Camera, 1999.*

Lee at al. "Development of a Portable 3CCD Camera System for Multispectral Imaging of Biological Samples", Oct. 21, 2014.*

Internet archive wayback machine for Nikon website "Understanding ISO Sensitivity",Mar. 20, 2017,http://web.archive.org/web/20170320015750/https://www.nikonusa.com/en/learn-and-explore/a/tips-and-techniques/understanding-iso-sensitivity.html.*

Office Action from Japan Patent Office (JPO) in Japanese Patent Appl. No. 2020-074282, dated Aug. 30, 2022, together with an English language translation.

* cited by examiner

FIG. 6

|  | FIRST CONFIGURATION EXAMPLE | SECOND CONFIGURATION EXAMPLE | THIRD CONFIGURATION EXAMPLE | FOURTH CONFIGURATION EXAMPLE | FIFTH CONFIGURATION EXAMPLE | SIXTH CONFIGURATION EXAMPLE |
|---|---|---|---|---|---|---|
| SECOND PRISM | VISIBLE LIGHT | VISIBLE LIGHT | IR LIGHT | UV LIGHT | VISIBLE LIGHT | VISIBLE LIGHT |
| THIRD PRISM | VISIBLE LIGHT | VISIBLE LIGHT | VISIBLE LIGHT | VISIBLE LIGHT | VISIBLE LIGHT | VISIBLE LIGHT |
| FIRST PRISM | IR LIGHT | IR LIGHT | IR LIGHT | IR LIGHT | VISIBLE LIGHT | UV LIGHT |

*FIG. 19*

| | SEVENTH CONFIGURATION EXAMPLE | EIGHTH CONFIGURATION EXAMPLE | NINTH CONFIGURATION EXAMPLE | TENTH CONFIGURATION EXAMPLE | ELEVENTH CONFIGURATION EXAMPLE |
|---|---|---|---|---|---|
| FOURTH PRISM | VISIBLE LIGHT | VISIBLE LIGHT | VISIBLE LIGHT | VISIBLE LIGHT | VISIBLE LIGHT |
| THIRD PRISM | VISIBLE LIGHT | UV LIGHT | VISIBLE LIGHT | VISIBLE LIGHT | VISIBLE LIGHT |
| SECOND PRISM | IV LIGHT | IR LIGHT | IR LIGHT | VISIBLE LIGHT | VISIBLE LIGHT |
| FIRST PRISM | IR LIGHT | IR LIGHT | IR LIGHT | IR LIGHT | UV LIGHT |

THREE-PLATE CAMERA AND FOUR-PLATE CAMERA

CROSS-REFERENCE TO RELATED APPLICATIONS

This application is based on and claims priority under 35 USC 119 from Japanese Patent Application No. 2020-074282 filed on Apr. 17, 2020, the contents of which are incorporated herein by reference.

TECHNICAL FIELD

The present disclosure relates to a three-plate camera and a four-plate camera.

BACKGROUND ART

In recent years, attention has been paid to a method of performing diagnosis in which at the time of surgery or examination, indocyanine green (ICG) is administered as a fluorescent reagent into a subject, ICG is excited by irradiation with excitation light or the like, and a near-infrared fluorescent image presented by ICG is imaged together with a subject image and is observed. For example, Patent Literature 1 discloses an imaging device including a blue color separation prism that reflects light of a blue component of incident light and a part of near-infrared light of a specific wavelength range and transmits the rest of light, a red color separation prism that reflects light of a red component and a part of near-infrared light of a specific wavelength range and transmits the rest of light, and a green color separation prism to which light transmitted through the red color separation prism is incident.

CITATION LIST

Patent Literature

Patent Literature 1: JP-A-2016-75825

SUMMARY OF INVENTION

In Patent Literature 1, a light amount of the part of near-infrared light of light from an affected part or the like is incident so as to be distributed to each of a plurality of color separation prisms and is imaged. For this reason, for example, there is a problem that light specialized for a wavelength range of the near-infrared light cannot be received by a corresponding imaging element. Therefore, at the time of surgery or examination described above, it is difficult to output a clearer fluorescent image of an observation part to which a fluorescent reagent is administered, and there is room for improvement in terms of making a doctor or the like more easily understand the affected part.

The present disclosure has been made in view of the above-described circumstances in the related art, and provides a three-plate camera and a four-plate camera that generate and output a clearer fluorescence image of an observation part to which a fluorescent reagent is administered, and support easy understanding of an affected part for a doctor or the like.

The present disclosure provides a three-plate camera including: an IR prism that causes an IR image sensor to receive incident IR light of light from an observation part; a visible prism that causes a visible image sensor to receive incident visible light of light from the observation part; a specific prism that causes a specific image sensor to receive incident light of a specific wavelength band of light from the observation part; and a video signal processing unit that generates an IR video signal, a visible video signal, and a specific video signal of the observation part based on respective imaging outputs of the IR image sensor, the visible image sensor, and the specific image sensor, combines the IR video signal, the visible video signal, and the specific video signal, and outputs a combined video signal to a monitor.

Further, the present disclosure provides a three-plate camera including: a first visible prism that causes a first visible image sensor to receive incident first visible light of light from an observation part; a second visible prism that causes a second visible image sensor to receive incident second visible light of light from the observation part; a specific prism that causes a specific image sensor to receive incident light of a specific wavelength band of light from the observation part; and a video signal processing unit that generates a first visible video signal, a second visible video signal, and a specific video signal of the observation part based on respective imaging outputs of the first visible image sensor, the second visible image sensor, and the specific image sensor, combines the first visible video signal, the second visible video signal, and the specific video signal, and outputs a combined video signal to a monitor.

Further, the present disclosure provides a four-plate camera including: an IR prism that causes an IR image sensor to receive incident IR light of light from an observation part; a visible prism that causes a visible image sensor to receive incident visible light of light from the observation part; a first specific prism that causes a first specific image sensor to receive incident light of a first specific wavelength band of light from the observation part; a second specific prism that causes a second specific image sensor to receive incident light of a second specific wavelength band of light from the observation part; and a video signal processing unit that generates an IR video signal, a visible video signal, a first specific video signal, and a second specific video signal of the observation part based on respective imaging outputs of the IR image sensor, the visible image sensor, the first specific image sensor, and the second specific image sensor, combines the IR video signal, the visible video signal, the first specific video signal, and the second specific video signal, and outputs a combined video signal to a monitor.

Further, the present disclosure provides a four-plate camera including: a first visible prism that causes a first visible image sensor to receive incident first visible light of light from an observation part; a second visible prism that causes a second visible image sensor to receive incident second visible light of light from the observation part; a first specific prism that causes a first specific image sensor to receive incident light of a first specific wavelength band of light from the observation part; a second specific prism that causes a second specific image sensor to receive incident light of a second specific wavelength band of light from the observation part; and a video signal processing unit that generates a first visible video signal, a second visible video signal, a first specific video signal, and a second specific video signal of the observation part based on respective imaging outputs of the first visible image sensor, the second visible image sensor, the first specific image sensor, and the second specific image sensor, combines the first visible video signal, the second visible video signal, the first specific video signal, and the second specific video signal, and outputs a combined video signal to a monitor.

According to the present disclosure, it is possible to generate and output a clearer fluorescent image of an observation part to which a fluorescent reagent is administered, and to support easy understanding of an affected part for a doctor or the like.

BRIEF DESCRIPTION OF DRAWINGS

FIG. 6 is a table illustrating a combination example of configuration examples of a three-plate camera according to a first embodiment.

FIG. 19 is a table illustrating a combination example of configuration examples of a four-plate camera according to a second embodiment.

DESCRIPTION OF EMBODIMENTS

Technical Background of Embodiments

Figure 1:
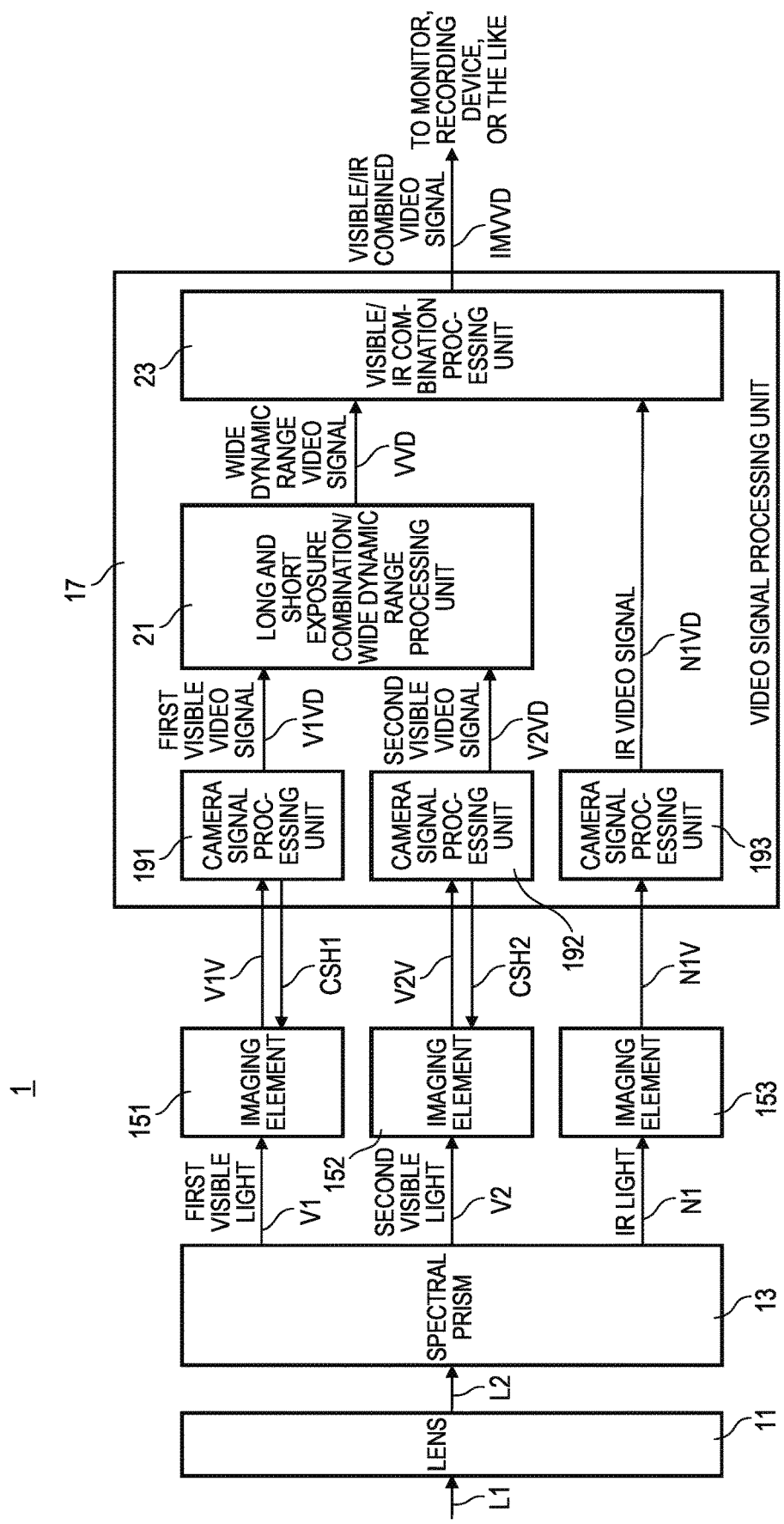
FIG. 1 is a block diagram illustrating an internal configuration example of a three-plate camera according to a first configuration example.

In Patent Literature 1, a light amount of a part of near-infrared light of light from an affected part or the like is incident so as to be distributed to each of a plurality of color separation prisms and is imaged. For this reason, for example, there is a problem that light specialized for a wavelength range of the near-infrared light cannot be received by a corresponding imaging element. Therefore, at the time of surgery or examination described above, it is difficult to output a clearer fluorescent image of an observation part to which a fluorescent reagent is administered, and there is room for improvement in terms of making a doctor or the like more easily understand the affected part.

Therefore, in the following first embodiment, an example of a three-plate camera will be described that generates and outputs a clearer fluorescent image of an observation part to which a fluorescent reagent is administered, and that supports easy understanding of an affected part for a doctor or the like.

In addition, Patent Literature 1 discloses a configuration in which a part of the near-infrared light is reflected in each of a plurality of prisms (specifically, a blue color separation prism and a red color separation prism) among prisms constituting a color separation prism, and is received by each corresponding image sensor at a subsequent stage. Therefore, visible light having a wavelength of about 400 nm to 800 nm cannot be reflected by the plurality of prisms constituting the color separation prism to be received by each corresponding image sensor at the subsequent stage, and it is difficult to obtain a clear imaged image having a high dynamic range. Therefore, there is room for improvement in terms of making the doctor or the like more easily understand the affected part at the time of surgery or examination described above.

Therefore, in the following first embodiment, an example of a three-plate camera will be described that generates and outputs a clearer imaged image of an observation part having a high dynamic range and that supports easy understanding of an affected part for a doctor or the like.

First Embodiment

Hereinafter, embodiments of a three-plate type camera and a four-plate type camera according to the present disclosure will be described in detail with reference to the drawings as appropriate. However, an unnecessarily detailed description may be omitted. For example, a detailed description of a well-known matter or a repeated description of substantially the same configuration may be omitted. This is to avoid unnecessary redundancy in the following description and to facilitate understanding for those skilled in the art. The accompanying drawings and the following description are provided for those skilled in the art to fully understand the present disclosure, and are not intended to limit the subject matter described in the claims.

First Configuration Example

In the first configuration example, it is assumed that a light amount of first visible light V1 incident on an imaging element 151 and a light amount of second visible light V2 incident on an imaging element 152 are different from each other.

FIG. 1 is a block diagram illustrating an internal configuration example of a three-plate camera 1 according to the first configuration example. The three-plate camera 1 includes a lens 11, a spectral prism 13, imaging elements 151, 152, and 153, and a video signal processing unit 17. The video signal processing unit 17 includes camera signal processing units 191, 192, and 193, a long and short exposure combination/wide dynamic range processing unit 21, and a visible/IR combination processing unit 23.

The three-plate camera (see FIGS. 1, 2 and 4) according to a first embodiment is used in, for example, a medical observation system that irradiates a fluorescent reagent (for example, indocyanine green that is abbreviated as "ICG" in the following description) administered in advance to an observation part (for example, an affected part) in a subject such as a patient with excitation light of a predetermined wavelength band (for example, 760 nm to 800 nm) at the time of surgery or examination, and that images the observation part emitting fluorescence at a long wavelength side (for example, 820 nm to 860 nm) based on the excitation light. An image (for example, a video of an observation part) imaged by the three-plate camera is displayed by a monitor MN1 (see FIG. 13), and supports execution of a medical practice by a user such as a doctor. Although an example in which the spectral prism 13 is used in, for example, the above-described medical observation system is described, the use thereof is not limited to medical applications and may be industrial applications.

Although not illustrated in FIG. 1, a tip end portion from the lens 11 of the three-plate camera 1 is configured with a scope that is to be inserted into an observation part (for example, an affected part. The same applies to the following). The scope is, for example, a main part of a medical instrument such as a rigid endoscope to be inserted into an observation part, and is an elongated light guide member capable of guiding light L1 from the observation part to the lens 11.

The lens 11 is attached on a target-facing side (tip end side) of the spectral prism 13, and concentrates the light L1 from the observation part (for example, reflected light at the observation part). Concentrated light L2 is incident on the spectral prism 13.

The spectral prism 13 as an example of an optical component receives the light L2 from the observation part, and disperses the light L2 into the first visible light V1, the second visible light V2, and IR light N1. The spectral prism 13 has a configuration in which a first prism 31 (for example, an IR prism), a second prism 32 (for example, a visible prism), and a third prism 33 (for example, a visible prism) are bonded in order (see FIG. 7). The first visible light V1 is incident on the imaging element 152 that is disposed so as to face the third prism 33. The second visible light V2 is incident on the imaging element 151 that is disposed so as to face the second prism 32. The IR light N1 is incident on the imaging element 153 that is disposed so as to face the first prism 31. A detailed example of a structure of the spectral prism 13 will be described later with reference to FIG. 7.

The imaging element 151 as an example of a visible image sensor includes, for example, a charge coupled device (CCD) or a complementary metal oxide semiconductor (CMOS) in which a plurality of pixels suitable for imaging of visible light are arranged, and an exposure control circuit (not illustrated) using an electronic shutter. The imaging element 151 is disposed so as to face the second prism 32 (for example, a visible prism) (see FIG. 7). The imaging element 151 performs imaging based on the first visible light V1 incident over first exposure time that is determined by the exposure control circuit based on an exposure control signal CSH1 from the camera signal processing unit 191. The imaging element 151 generates a video signal V1V of the observation part by imaging, and outputs the video signal V1V to the video signal processing unit 17.

The imaging element 152 as an example of a specific image sensor includes, for example, a CCD or CMOS in which a plurality of pixels suitable for imaging of visible light are arranged, and an exposure control circuit (not illustrated) using an electronic shutter. The imaging element 152 is disposed so as to face the third prism 33 (for example, a visible prism) (see FIG. 7). The imaging element 152 performs imaging based on the second visible light V2 incident over second exposure time that is determined by the exposure control circuit based on an exposure control signal CSH2 from the camera signal processing unit 192. The imaging element 152 generates a video signal V2V of the observation part by imaging, and outputs the video signal V2V to the video signal processing unit 17.

The imaging element 153 as an example of an IR image sensor includes, for example, a CCD or a CMOS in which a plurality of pixels suitable for imaging of IR light are arranged. The imaging element 153 is disposed so as to face the first prism 31 (for example, an IR prism) (see FIG. 7). The imaging element 153 performs imaging based on the incident IR light N1. The imaging element 153 generates a video signal N1V of the observation part by imaging, and outputs the video signal N1V to the video signal processing unit 17.

The video signal processing unit 17 is configured with a processor such as a digital signal processor (DSP) or a field-programmable gate array (FPGA), for example. Each of the camera signal processing units 191 to 193, the long and short exposure combination/wide dynamic range processing unit 21, and the visible/IR combination processing unit 23 is implemented by the processor described above.

The camera signal processing unit 191 performs various types of camera signal processing using the video signal V1V from the imaging element 151 to generate a first visible video signal V1VD of the observation part, and outputs the first visible video signal V1VD to the long and short exposure combination/wide dynamic range processing unit 21. In addition, the camera signal processing unit 191 generates the exposure control signal CSH1 for determining the first exposure time of the imaging element 151 and outputs the generated exposure control signal CSH1 to the imaging element 151. The imaging element 151 controls the first exposure time of the first visible light V1 based on the exposure control signal CSH1.

The camera signal processing unit 192 performs various types of camera signal processing using the video signal V2V from the imaging element 152 to generate a second visible video signal V2VD of the observation part, and outputs the second visible video signal V2VD to the long and short exposure combination/wide dynamic range processing unit 21. Here, in the first configuration example, the light amount of the first visible light V1 incident on the imaging element 151 is different from the light amount of the second visible light V2 incident on the imaging element 152. Therefore, the first visible video signal V1VD from the camera signal processing unit 191 and the second visible video signal V2VD from the camera signal processing unit 192 are different in brightness (sensitivity). In addition, the camera signal processing unit 192 generates the exposure control signal CSH2 for determining the second exposure time of the imaging element 152 and outputs the generated exposure control signal CSH2 to the imaging element 152. The imaging element 152 controls the second exposure time of the second visible light V2 based on the exposure control signal CSH2. Although details will be described later, the first exposure time and the second exposure time may be the same or different.

The camera signal processing unit 193 performs various types of camera signal processing using the video signal N1V from the imaging element 153 to generate an IR video signal N1VD of the observation part, and outputs the IR video signal N1VD to the visible/IR combination processing unit 23.

The long and short exposure combination/wide dynamic range processing unit 21 receives the two video signals having different brightness (sensitivity) (specifically, the first visible video signal V1VD from the camera signal processing unit 191 and the second visible video signal V2VD from the camera signal processing unit 192) and combines the two video signals by superimposition, and generates a wide dynamic range video signal VVD. That is, the long and short exposure combination/wide dynamic range processing unit 21 can generate the wide dynamic range video signal VVD whose dynamic range is wider than that of the first visible video signal V1VD or the second visible video signal V2VD by combining the first visible video signal V1VD and the second visible video signal V2VD having different brightness (sensitivity). The long and short exposure combination/wide dynamic range processing unit 21 outputs the wide dynamic range video signal VVD to the visible/IR combination processing unit 23.

The visible/IR combination processing unit 23 receives the wide dynamic range video signal VVD from the long and short exposure combination/wide dynamic range processing unit 21 and the IR video signal N1VD from the camera signal processing unit 193, and combines the wide dynamic range video signal VVD and the IR video signal N1VD by superimposition, and generates a visible/IR combined video signal IMVVD. The visible/IR combination processing unit 23 may output the visible/IR combined video signal IMVVD to the monitor MN1 or transmit the visible/IR combined video signal IMVVD to a recording device (not illustrated) for accumulation.

The monitor MN1 constitutes, for example, an image console (not illustrated) disposed in an operating room at the time of surgery or examination, and displays the visible/IR combined video signal IMVVD of the observation part that is generated by the three-plate camera 1. Accordingly, the user, such as a doctor, visually recognizes the visible/IR combined video signal IMVVD displayed on the monitor MN1, and thus can understand in detail a condition of a surrounding portion of a surgical field or the like according to a color video having the wide dynamic range as well as a condition of a part emitting fluorescence in the observation part. The recording device is, for example, a recorder capable of recording data of the visible/IR combined video signal IMVVD generated by the three-plate camera 1.

Second Configuration Example

In a second configuration example, it is assumed that the light amount of the first visible light V1 incident on the imaging element 151 and the light amount of the second visible light V2 incident on the imaging element 152 are substantially equal (in other words, there is little difference). Therefore, the first visible video signal V1VD from the camera signal processing unit 191 and the second visible video signal V2VD from the camera signal processing unit 192 are substantially the same in brightness (sensitivity), and the first visible video signal V1VD and the second visible video signal V2VD having substantially the same brightness (sensitivity) are subjected to combination processing corresponding to pixel shift, so that a high-resolution video signal VVDA having high resolution can be generated.

Figure 2:
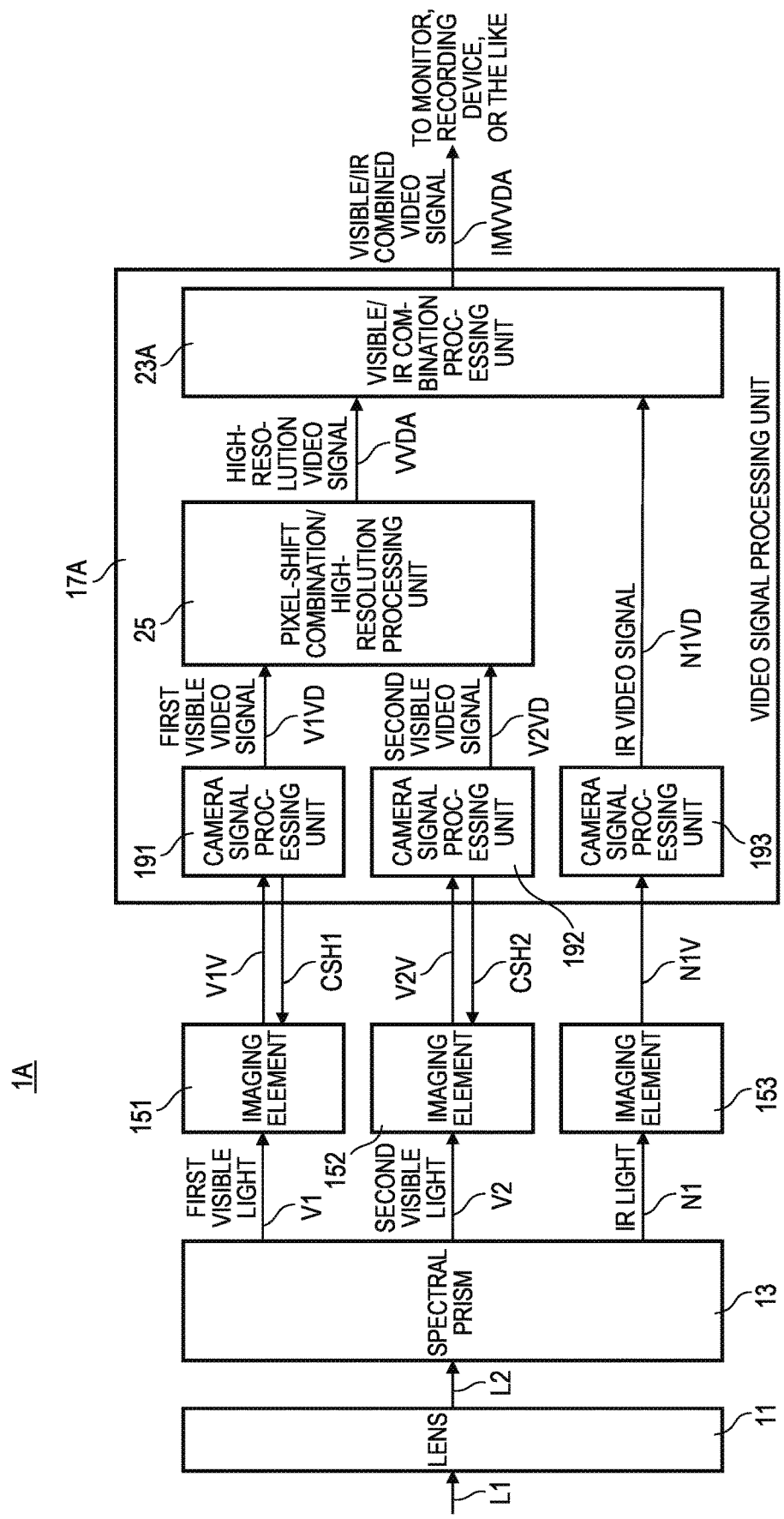
FIG. 2 is a block diagram illustrating an internal configuration example of a three-plate camera according to a second configuration example.

FIG. 2 is a block diagram illustrating an internal configuration example of a three-plate camera 1A according to the second configuration example. The three-plate camera 1A includes the lens 11, the spectral prism 13, the imaging elements 151, 152, and 153, and a video signal processing unit 17A. The video signal processing unit 17A includes the camera signal processing units 191, 192, and 193, a pixel-shift combination/high-resolution processing unit 25, and a visible/IR combination processing unit 23A. In the description of FIG. 2, the same components as those in FIG. 1 are denoted by the same reference signs, and a description thereof will be simplified or omitted, and different contents will be described. In the description of a configuration in which the three-plate camera according to the first embodiment described below is capable of imaging at least two channels of visible light (specifically, the first configuration example, the second configuration example, a fifth configuration example, and a sixth configuration example), the long and short exposure combination/wide dynamic range processing unit 21 and the like may not only perform processing for having a color video having a wide dynamic range described in the first configuration example, but also perform the high-resolution processing (see the above description) performed by the pixel-shift combination/high-resolution processing unit 25 in the second configuration example. Further, in the description of the configuration in which the three-plate camera according to the first embodiment described below is capable of imaging at least two channels of visible light (see the above description), the pixel-shift combination/high-resolution processing unit 25 may be used in place of the long and short exposure combination/wide dynamic range processing unit 21 and the like.

In the three-plate camera 1A, a high-resolution video signal VVDA by pixel shift is generated in the video signal processing unit 17A. For this reason, in the spectral prism 13, when the imaging element 151 on which the first visible light V1 is incident and the imaging element 152 on which the second visible light V2 is incident are bonded to the second prism 32 and third prism 33 correspondingly, it is necessary to bond the imaging element 151 and the imaging element 152 to each other such that positions thereof are shifted by an optically half pixel (for example, in a horizontal direction or in a vertical direction or in both directions). Accordingly, the high-resolution video signal VVDA by pixel shift can be generated in the pixel-shift combination/high-resolution processing unit 25 based on imaging of the imaging elements 151 and 152 that are arranged to be shifted by an optically half pixel (see the above description).

The camera signal processing unit 191 generates the first visible video signal V1VD of the observation part, and outputs the first visible video signal V1VD to the pixel-shift combination/high-resolution processing unit 25.

The camera signal processing unit 192 generates the second visible video signal V2VD of the observation part, and outputs the second visible video signal V2VD to the pixel-shift combination/high-resolution processing unit 25.

The pixel-shift combination/high-resolution processing unit 25 receives the two video signals having substantially the same brightness (sensitivity) (specifically, the first visible video signal V1VD from the camera signal processing unit 191 and the second visible video signal V2VD from the camera signal processing unit 192) as described above. The pixel-shift combination/high-resolution processing unit 25 performs combination processing of the two received video signals (that is, combination of the first visible video signal V1VD generated by the camera signal processing unit 191 based on the imaging of the imaging element 151 bonded to the second prism 32 and the second visible video signal V2VD generated by the camera signal processing unit 192 based on the imaging of the imaging element 152 bonded to the third prism 33), and generates the high-resolution video signal VVDA. The pixel-shift combination/high-resolution processing unit 25 can generate the high-resolution video signal VVDA having a higher resolution than the first visible video signal V1VD or the second visible video signal V2VD by performing the combination processing (see the above description) of the two received video signals. The pixel-shift combination/high-resolution processing unit 25 outputs the high-resolution video signal VVDA to the visible/IR combination processing unit 23A.

The visible/IR combination processing unit 23A receives the high-resolution video signal VVDA from the pixel-shift combination/high-resolution processing unit 25 and the IR video signal N1VD from the camera signal processing unit 193 and combines the two signals by superimposition, and generates a visible/IR combined video signal IMVVDA. The visible/IR combination processing unit 23A may output the visible/IR combined video signal IMVVDA to the monitor MN1 or transmit the visible/IR combined video signal IMVVDA to a recording device (not illustrated) for accumulation.

Third Configuration Example

Figure 3:
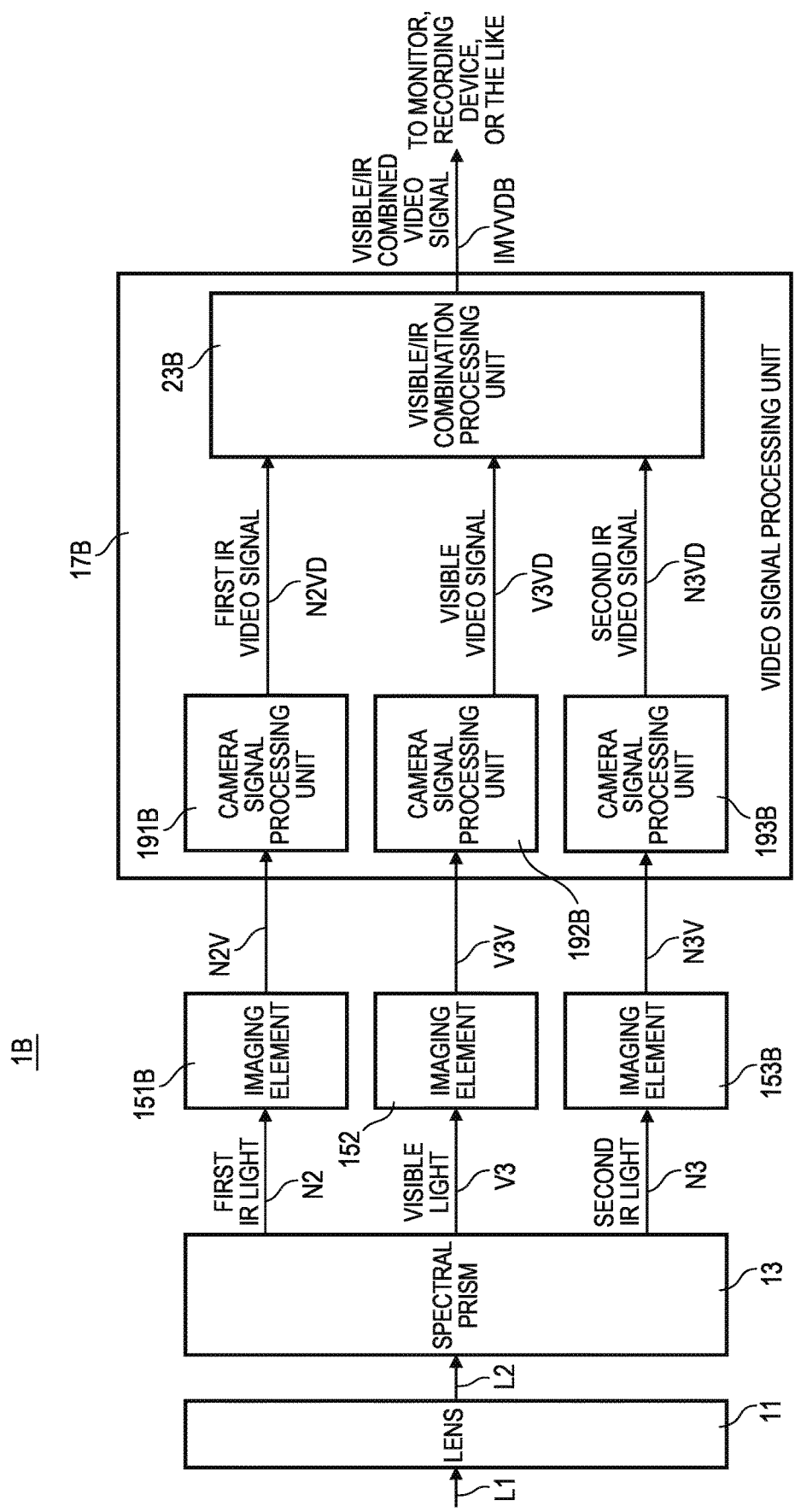
FIG. 3 is a block diagram illustrating an internal configuration example of a three-plate camera according to a third configuration example.

In a third configuration example, it is assumed that imaging is performed by using an imaging element capable of imaging each of two different wavelength bands among wavelength bands of near-infrared (IR) light using two channels (for example, imaging elements 151B and 153B illustrated in FIG. 3). Therefore, by appropriately superimposing a first IR video signal N2VD based on first IR light N2 imaged by the imaging element 151B and a second IR video signal N3VD based on second IR light N3 imaged by the imaging element 153B, it is possible to generate a video signal that allows identifying a more detailed state of an affected part as compared with a configuration (for example, the first configuration example and the second configuration example) in which the IR light is imaged only by one channel.

FIG. 3 is a block diagram illustrating an internal configuration example of a three-plate camera 1B according to the third configuration example. The three-plate camera 1B includes the lens 11, the spectral prism 13, the imaging elements 151B, 152, and 153B, and a video signal processing unit 17B. The video signal processing unit 17B includes camera signal processing units 191B, 192B, and 193B, and a visible/IR combination processing unit 23B. In the description of FIG. 3, the same components as those in FIG. 1 or 2 are denoted by the same reference signs, and a description thereof will be simplified or omitted, and different contents will be described.

The three-plate camera 1B is used in, for example, a medical observation system that irradiates a plurality of types of fluorescent reagents (for example, ICG) administered in advance to observation parts (for example, an affected part) in a subject such as a patient with excitation light of a predetermined wavelength band at the time of surgery or examination, and that images the observation parts emitting fluorescence at a long wavelength side (for example, 700 nm to 800 nm and 800 nm to 900 nm) based on the excitation light. An image (for example, a video of an observation part) imaged by the three-plate camera 1B is displayed by the monitor MN1 (see FIG. 14), and supports execution of a medical practice by a user such as a doctor.

The spectral prism 13 receives the light L2 from the observation part, and disperses the light L2 into the first IR light N2, visible light V3, and the second IR light N3. The spectral prism 13 has a configuration in which the first prism 31 (for example, an IR prism), the second prism 32 (for example, an IR prism), and the third prism 33 (for example, a visible prism) are bonded in order (see FIG. 7). The first IR light N2 is incident on the imaging element 151B that is disposed so as to face the second prism 32. The visible light V3 is incident on the imaging element 152 that is disposed so as to face the third prism 33. The second IR light N3 is incident on the imaging element 153B that is disposed so as to face the first prism 31. A detailed example of a structure of the spectral prism 13 will be described later with reference to FIG. 7.

The imaging element 151B as an example of an IR image sensor includes, for example, a CCD or a CMOS in which a plurality of pixels suitable for imaging of IR light are arranged. The imaging element 151B is disposed so as to face the second prism 32 (for example, an IR prism) (see FIG. 7). The imaging element 151B performs imaging based on the incident first IR light N2. The imaging element 151B generates a video signal N2V of the observation part by imaging, and outputs the video signal N2V to the video signal processing unit 17B.

The imaging element 153B as an example of an IR image sensor includes, for example, a CCD or a CMOS in which a plurality of pixels suitable for imaging of IR light are arranged. The imaging element 153B is disposed so as to face the first prism 31 (for example, an IR prism) (see FIG. 7). The imaging element 153B performs imaging based on the incident second IR light N3. The imaging element 153B generates a video signal N3V of the observation part by imaging, and outputs the video signal N3V to the video signal processing unit 17B.

The video signal processing unit 17B is configured with a processor such as a DSP or an FPGA, for example. Each of the camera signal processing units 191B to 193B and the visible/IR combination processing unit 23B is implemented by the processor described above.

The camera signal processing unit 191B performs various types of camera signal processing using the video signal N2V from the imaging element 151B to generate the IR video signal N2VD of the observation part, and outputs the IR video signal N2VD to the visible/IR combination processing unit 23B. Although details will be described later, the first IR video signal N2VD and the second IR video signal N3VD have different wavelengths of incident light used for imaging (see FIGS. 8D and 8E).

The camera signal processing unit 192B performs various types of camera signal processing using a video signal V3V from the imaging element 152 to generate a visible video signal V3VD of the observation part, and outputs the visible video signal V3VD to the visible/IR combination processing unit 23B.

The camera signal processing unit 193B performs various types of camera signal processing using the video signal N3V from the imaging element 153B to generate the second IR video signal N3VD of the observation part, and outputs the second IR video signal N3VD to the visible/IR combination processing unit 23B.

The visible/IR combination processing unit 23B receives the first IR video signal N2VD from the camera signal processing unit 191B, the visible video signal V3VD from the camera signal processing unit 192B, and the second IR video signal N3VD from the camera signal processing unit 193B, and combines the three signals by superimposition, and generates a visible/IR combined video signal IMVVDB. The visible/IR combination processing unit 23B may output the visible/IR combined video signal IMVVDB to the monitor MN1 or transmit the visible/IR combined video signal IMVVDB to a recording device (not illustration) for accumulation.

Fourth Configuration Example

In a fourth configuration example, it is assumed that imaging is performed by using an imaging element capable of imaging a plurality of different wavelength bands of visible light, IR light, and ultra violet (UV) light using three channels. Therefore, by superimposing video signals imaged by imaging elements 151C, 152, and 153, it is possible to generate a video signal that allows identifying a detailed state of an affected part by imaging of light in various wavelength bands.

Figure 4:
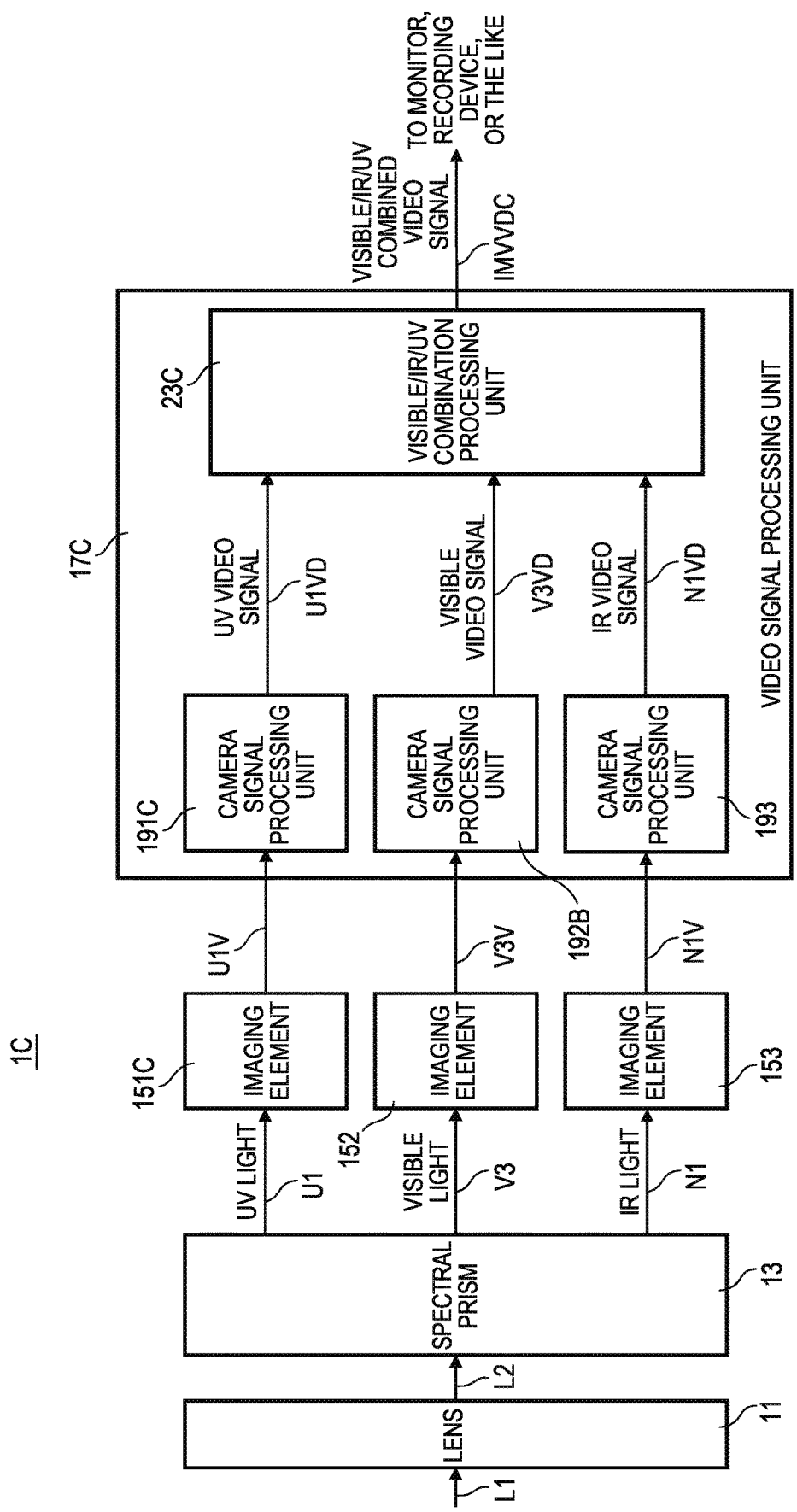
FIG. 4 is a block diagram illustrating an internal configuration example of a three-plate camera according to a fourth configuration example.

FIG. 4 is a block diagram illustrating an internal configuration example of a three-plate camera 1C according to the fourth configuration example. The three-plate camera 1C includes the lens 11, the spectral prism 13, the imaging elements 151C, 152, and 153, and a video signal processing unit 17C. The video signal processing unit 17C includes camera signal processing units 191C, 192B, and 193, and a visible/IR combination processing unit 23C. In the description of FIG. 4, the same components as those in FIGS. 1 to 3 are denoted by the same reference signs, and a description thereof will be simplified or omitted, and different contents will be described.

The spectral prism 13 receives the light L2 from an observation part, and disperses the light L2 into UV light U1, the visible light V3, and the IR light N1. The spectral prism 13 has a configuration in which the first prism 31 (for example, an IR prism), the second prism 32 (for example, an UV prism), and the third prism 33 (for example, a visible prism) are bonded in order (see FIG. 7). The UV light U1 is incident on the imaging element 151C that is disposed so as to face the second prism 32. The visible light V3 is incident on the imaging element 152 that is disposed so as to face the third prism 33. The IR light N1 is incident on the imaging element 153 that is disposed so as to face the first prism 31.

A detailed example of a structure of the spectral prism 13 will be described later with reference to FIG. 7.

The imaging element 151C as an example of a specific image sensor includes, for example, a CCD or a CMOS in which a plurality of pixels suitable for imaging of UV light are arranged. The imaging element 151C is disposed so as to face the second prism 32 (for example, a UV prism) (see FIG. 7). The imaging element 151C performs imaging based on the incident UV light U1. The imaging element 151C generates a video signal U1V of the observation part by imaging, and outputs the video signal U1V to the video signal processing unit 17C.

The video signal processing unit 17C is configured with a processor such as a DSP or an FPGA, for example. Each of the camera signal processing units 191C, 192B and 193 and the visible/IR combination processing unit 23C is implemented by the processor described above.

The camera signal processing unit 191C performs various types of camera signal processing using the video signal U1V from the imaging element 151C to generate a UV video signal U1VD of the observation part, and outputs the UV video signal U1VD to the visible/IR combination processing unit 23C.

The visible/IR combination processing unit 23C receives the UV video signal U1VD from the camera signal processing unit 191C, the visible video signal V3VD from the camera signal processing unit 192B, and the IR video signal N1VD from the camera signal processing unit 193 and combines the three signals by superimposition, and generates a visible/IR combined video signal IMVVDC. The visible/IR combination processing unit 23C may output the visible/IR combined video signal IMVVDC to the monitor MN1 or transmit the visible/IR combined video signal IMVVDC to a recording device (not illustration) for accumulation.

Fifth Configuration Example

Figure 5:
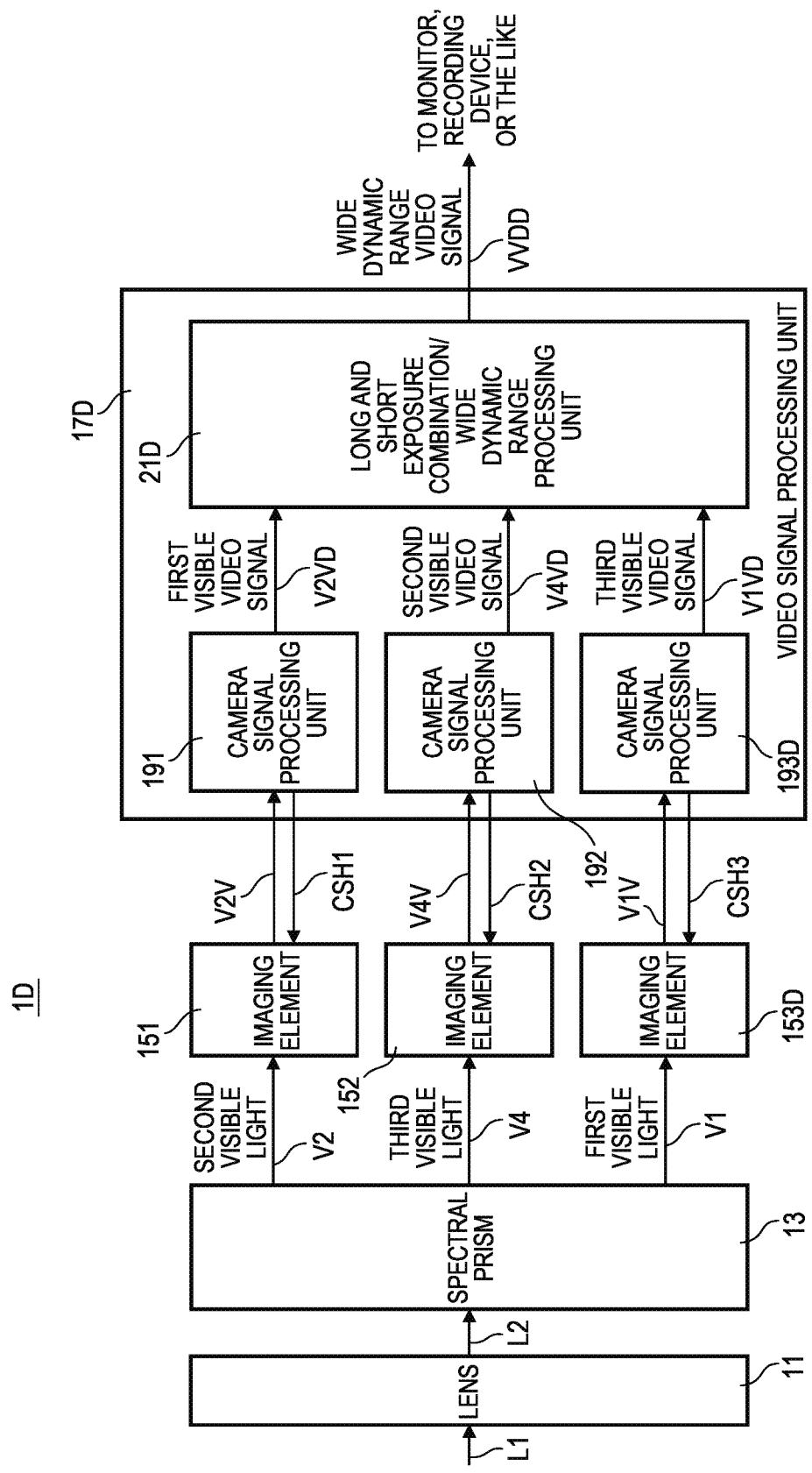
FIG. 5 is a block diagram illustrating an internal configuration example of a three-plate camera according to a fifth configuration example.

In a fifth configuration example, it is assumed that imaging is performed by using an imaging element capable of imaging a wavelength band of visible light using three channels (for example, imaging elements 151, 152, and 153D illustrated in FIG. 5), and light amounts of visible light incident on respective imaging elements are different from each other. Accordingly, it is possible to generate a video signal that allows identifying in detail a condition of a surrounding portion of a surgical field or the like according to a color video having an observation part or a high dynamic range in a periphery thereof.

FIG. 5 is a block diagram illustrating an internal configuration example of a three-plate camera 1D according to the fifth configuration example. The three-plate camera 1D includes the lens 11, the spectral prism 13, imaging elements 151, 152, and 153D, and a video signal processing unit 17D. The video signal processing unit 17D includes camera signal processing units 191, 192, and 193D and a long and short exposure combination/wide dynamic range processing unit 21D. In the description of FIG. 5, the same components as those in FIGS. 1 to 4 are denoted by the same reference signs, and a description thereof will be simplified or omitted, and different contents will be described.

The three-plate camera 1D is used in, for example, a medical observation system that obtains a more clear image of an observation part (for example, an affected part) in a subject such as a patient or a surgical field of a periphery thereof than a normal color video (in other words, having a higher dynamic range than a normal color video) at the time of surgery or examination. An image (for example, a video of the observation part) imaged by the three-plate camera 1D is displayed by the monitor MN1, and supports execution of a medical practice by a user such as a doctor.

The spectral prism 13 receives the light L2 from the observation part and disperses the light L2 into the first visible light V1, the second visible light V2, and third visible light V4. The spectral prism 13 has a configuration in which the first prism 31 (for example, a visible prism), the second prism 32 (for example, a visible prism), and the third prism 33 (for example, a visible prism) are bonded in order (see FIG. 7). The first visible light V1 is incident on the imaging element 153D that is disposed so as to face the first prism 31 (for example, a visible prism). The second visible light V2 is incident on the imaging element 151 that is disposed so as to face the second prism 32 (for example, a visible prism). The third visible light V4 is incident on the imaging element 152 that is disposed so as to face the third prism 33 (for example, a visible prism). A detailed example of a structure of the spectral prism 13 will be described later with reference to FIG. 7.

The imaging element 153D as an example of a first visible image sensor includes, for example, a CCD or a CMOS in which a plurality of pixels suitable for imaging of visible light are arranged. The imaging element 153D is disposed so as to face the first prism 31 (for example, an example of a first visible prism) (see FIG. 7). The imaging element 153D performs imaging based on the incident first visible light V1. The imaging element 153D generates the video signal V1V of the observation part by imaging, and outputs the video signal V1V to the video signal processing unit 17D.

The imaging element 151 as an example of a second visible image sensor includes, for example, a CCD or a CMOS in which a plurality of pixels suitable for imaging of visible light are arranged. The imaging element 151 is disposed so as to face the second prism 32 (an example of the second visible prism) (see FIG. 7). The imaging element 151 performs imaging based on the incident second visible light V2. The imaging element 151 generates the video signal V2V of the observation part by imaging, and outputs the video signal V2V to the video signal processing unit 17D.

The imaging element 152 as an example of a specific image sensor includes, for example, a CCD or a CMOS in which a plurality of pixels suitable for imaging of visible light are arranged. The imaging element 152 is disposed so as to face the third prism 33 (an example of a specific prism) (see FIG. 7). The imaging element 152 performs imaging based on the incident third visible light V4. The imaging element 152 generates a video signal V4V of the observation part by imaging, and outputs the video signal V4V to the video signal processing unit 17D.

The video signal processing unit 17D is configured with a processor such as a DSP or an FPGA, for example. Each of the camera signal processing units 191, 192, and 193D and the long and short exposure combination/wide dynamic range processing unit 21D is implemented by the processor described above.

The camera signal processing unit 193D performs various types of camera signal processing using the video signal V1V from the imaging element 153D to generate a third visible video signal V1VD of the observation part, and outputs the third visible video signal V1VD to the long and short exposure combination/wide dynamic range processing unit 21D. In addition, the camera signal processing unit 193D generates an exposure control signal CSH3 for determining third exposure time of the imaging element 153D and outputs the generated exposure control signal CSH3 to the imaging element 153D. The imaging element 153D controls the third exposure time of the first visible light V1 based on the exposure control signal CSH3.

The long and short exposure combination/wide dynamic range processing unit 21D receives three video signals having different brightness (sensitivity) (specifically, a first visible video signal V2VD from the camera signal processing unit 191, a second visible video signal V4VD from the camera signal processing unit 192, and the third visible video signal V1VD from the camera signal processing unit 193D) and combines the three video signals by superimposition, and generates a wide dynamic range video signal VVDD. That is, by combining the first visible video signal V2VD, the second visible video signal V4VD, and the third visual video signal V1VD having different brightness (sensitivity), the long and short exposure combination/wide dynamic range processing unit 21D can generate the wide dynamic range video signal VVDD having a wider dynamic range than the first visible video signal V2VD, the second visible video signal V4VD, or the third visible video signal V1VD. The long and short exposure combination/wide dynamic range processing unit 21D may output the wide dynamic range video signal VVDD to the monitor MN1 or transmit the wide dynamic range video signal VVDD to a recording device (not illustrated) for accumulation.

FIG. 6 is a table illustrating a combination example of configuration examples of the three-plate camera according to the first embodiment. In FIG. 6, the first configuration example is described with reference to FIG. 1, the second configuration example is described with reference to FIG. 2, the third configuration example is described with reference to FIG. 3, the fourth configuration example is described with reference to FIG. 4, and the fifth configuration example is described with reference to FIG. 5. As the three-plate camera according to the first embodiment, as a modification of the first configuration example or the second configuration example (that is, a sixth configuration example), the light incident on the first prism 31 may be UV light. That is, in the description of FIGS. 1 and 2, the "IR light" may be replaced with "UV light", the "video signal N1V" may be replaced with "video signal U1V", and the "IR video signal N1VD" may be replaced with "UV video signal U1VD".

Figure 7:
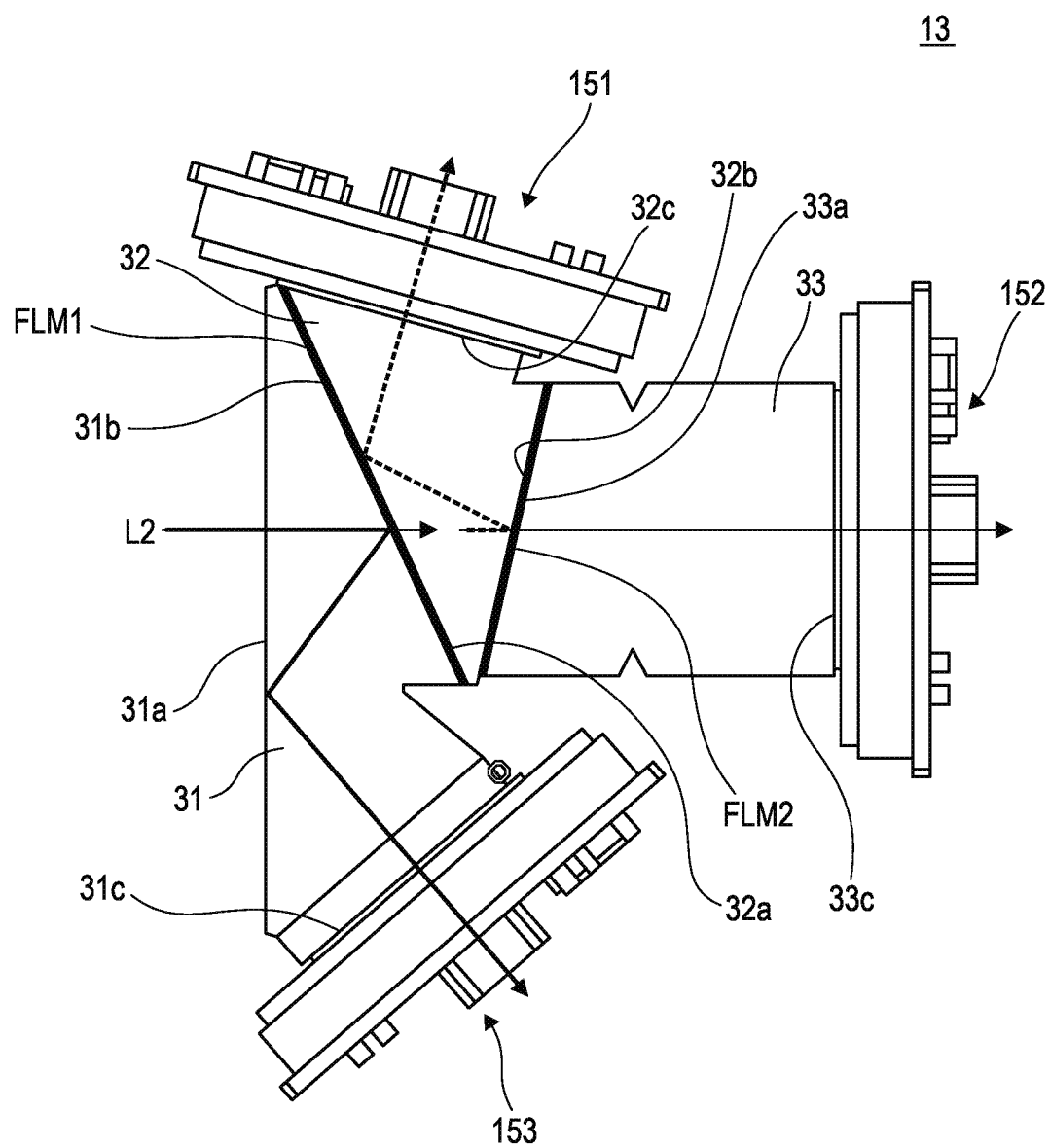
FIG. 7 is a diagram illustrating an example of a structure of a spectral prism according to the first embodiment.

FIG. 7 is a diagram illustrating an example of a structure of the spectral prism 13 according to the first embodiment. As described above, the spectral prism 13 has a configuration in which the first prism 31, the second prism 32, and the third prism 33 are bonded in this order. The first prism 31, the second prism 32, and the third prism 33 are assembled in order in an optical axis direction of the light L2 concentrated by the lens 11. Here, the optical axis direction is a direction in which the light L2 is incident perpendicularly on an incidence surface 31a of the first prism 31. In the first configuration example to the sixth configuration example described above, the roles (in other words, functions and applications) of the first prism 31, the second prism 32, and the third prism 33 may be the same or different.

First, the first prism 31 is exemplified as an IR prism (see the first to fourth configuration examples). However, the first prism 31 is not limited to an IR prism, and may be a visible prism (see the fifth configuration example) or a UV prism (see the sixth configuration example).

The IR prism includes the incidence surface 31a on which the light L2 is incident, a reflecting surface 31b on which a first reflecting film FLM1 (for example, a dichroic mirror) for reflecting IR light in the light L2 is formed, and an emission surface 31c from which the IR light is emitted. The first reflecting film FLM1 is formed on the reflecting surface 31b by vapor deposition or the like, and reflects IR light (for example, IR light in a wavelength band of 800 nm or more) in the light L2, and transmits light (for example, UV light of about 300 nm to 400 nm or visible light of about 400 nm to 800 nm) that is not the IR light in the light L2 (see FIG. 8A). The IR light is totally reflected by the incidence surface 31a after being reflected by the reflecting surface 31b, and is incident on the imaging element 153 through the emission surface 31c. In this way, since the IR prism is disposed as the first prism 31, the IR component light in the light L2 from an observation part is imaged on the most target-facing side (that is, the observation part side) of the spectral prism 13. Compared with a case where the IR component light is imaged at a rear stage side (that is, a base end side) of the spectral prism 13, attenuation of a light amount due to reflection or the like does not occur, and a condition of an affected part based on fluorescence emission of a fluorescent reagent can be more clearly identified.

Figure 8A:
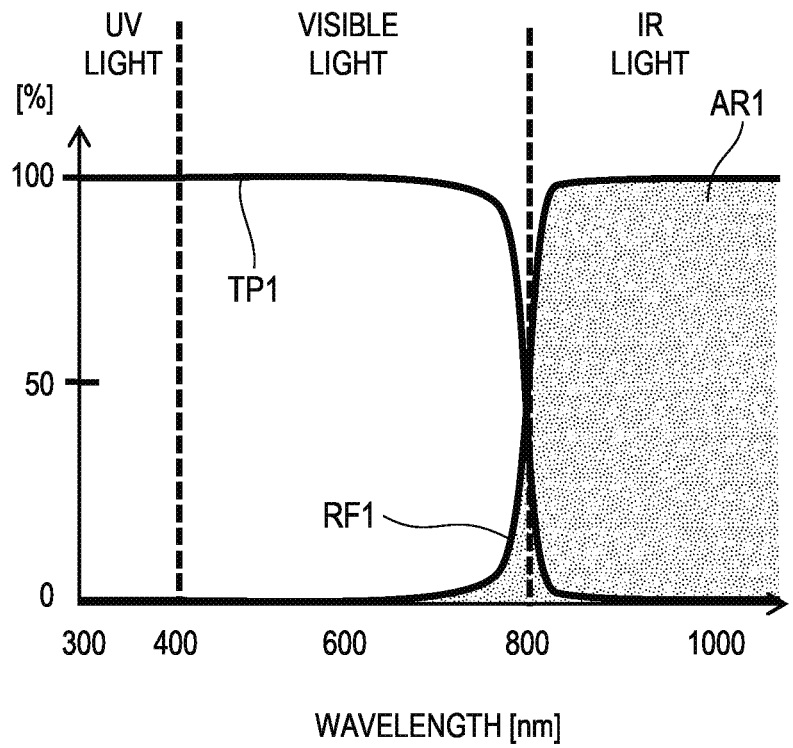
FIG. 8A is a graph illustrating an example of a spectral characteristic of a first reflecting film.

FIG. 8A is a graph illustrating an example of a spectral characteristic of the first reflecting film FLM1. In FIG. 8A, the horizontal axis represents wavelength [nm: nanometers], and the vertical axis represents reflectance or transmittance. A characteristic TP1 indicates the transmittance of the first reflecting film, and according to the characteristic TP1, the first reflecting film FLM1 can transmit light of about 300 nm to 800 nm. A characteristic RF1 indicates the reflectance of the first reflecting film FLM1, and according to the characteristic RF1, the first reflecting film FLM1 can reflect IR light of 800 nm or more. Therefore, all of the IR light of a light amount represented by area AR1 (in other words, the IR light in the light L2) can be incident on the imaging element 153.

Next, the second prism 32 is exemplified as a visible prism (see the first, second, fifth, and sixth configuration examples). However, the second prism 32 is not limited to a visible prism, and may be an IR prism (see the third configuration example) or a UV prism (see the fourth configuration example).

The visible prism includes an incidence surface 32a on which light transmitted through the first reflecting film FLM1 is incident, a reflecting surface 32b on which a second reflecting film FLM2 (for example, a beam splitter) for reflecting a light amount of a part of the transmitted light is formed, and an emission surface 32c through which reflected visible light of the light amount of the part of the transmitted light is emitted. The second reflecting film FLM2 is formed on the reflecting surface 32b by vapor deposition or the like, reflects visible light having a light amount of a part of visible light incident on the incidence surface 32a (for example, about 20% of the light incident on the incidence surface 32a), and transmits visible light having the remaining light amount (for example, about 80% of the light incident on the incidence surface 32a) (see FIG. 8B). The part of visible light is totally reflected by the incidence surface 32a after being reflected by the reflecting surface 32b, and is incident on the imaging element 151 through the emission surface 32c. The proportion of the visible light reflected by the second reflecting film FLM2 is not limited to 20%, and may be, for example, in a range of about 1% to 30%.

Figure 8B:
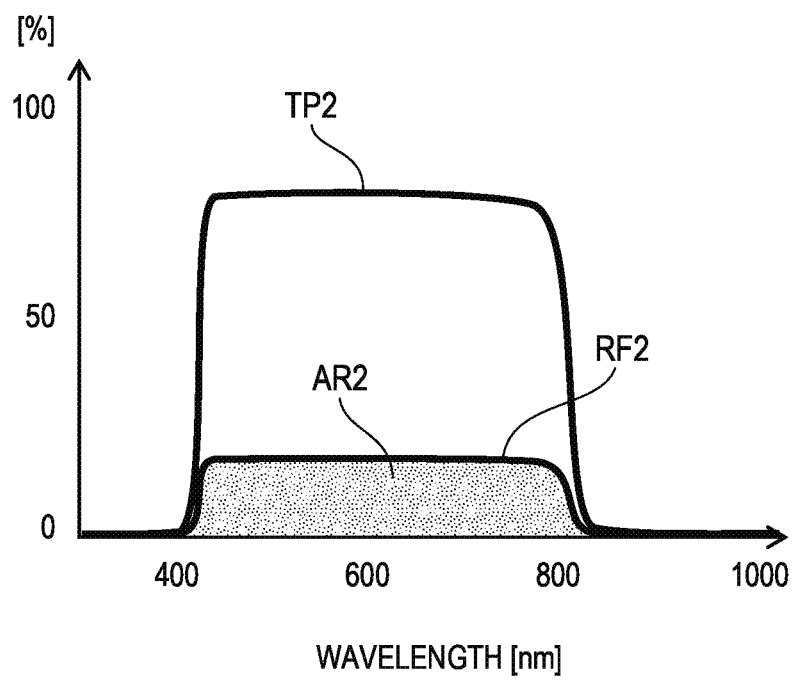
FIG. 8B is a graph illustrating an example of a spectral characteristic of a second reflecting film.

FIG. 8B is a graph illustrating an example of a spectral characteristic of the second reflecting film FLM2. In FIG. 8B, the horizontal axis represents wavelength [nm: nanometers], and the vertical axis represents reflectance or transmittance. A characteristic TP2 indicates the transmittance of the second reflecting film, and according to the characteristic TP2, the second reflecting film FLM2 can transmit 80% of the visible light of about 400 nm to 800 nm. A characteristic RF2 indicates the reflectance of the second reflecting film FLM2, and according to the characteristic RF2, the second reflecting film FLM2 can reflect 20% of visible light of about 400 to 800 nm. Therefore, visible light of a light amount indicated by area AR2 (that is, 20% of visible light (100%) incident on the incidence surface 32a) can be incident on the imaging element 151. In a case where the third prism 33, which will be described later, is a visible prism, the 80% visible light transmitted through the second reflecting film FLM2 transmits through the third prism 33 and be incident on the imaging element 152.

In the spectral prism 13 corresponding to the second configuration example (see FIG. 2), the second reflecting film FLM2 reflects visible light having a light amount of a part of visible light incident on the incidence surface 32a (for example, about 50% of the light incident on the incidence surface 32a), and transmits visible light having the remaining light amount (for example, about 50% of the light incident on the incidence surface 32a). The proportion of the visible light reflected by the second reflecting film FLM2 in this case is not limited to 50%, and may be, for example, in a range of about 30% to 50%. Similarly, in a case where the third prism 33, which will be described later, is a visible prism, the 50% visible light transmitted through the second reflecting film FLM2 transmits through the third prism 33 and is incident on the imaging element 152.

Figure 8C:
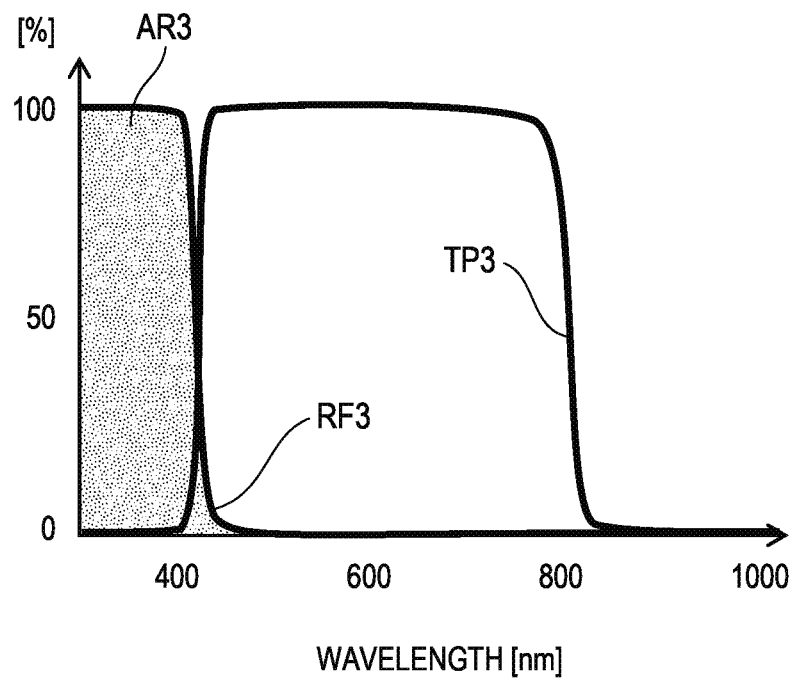
FIG. 8C is a graph illustrating another example of the spectral characteristic of the first reflecting film or the second reflecting film.

FIG. 8C is a graph illustrating another example of the spectral characteristic of the first reflecting film or the second reflecting film. In FIG. 8C, the horizontal axis represents wavelength [nm: nanometers], and the vertical axis represents reflectance or transmittance. A characteristic TP3 indicates the transmittance of the first reflecting film or the second reflecting film, and according to the characteristic TP3, the first reflecting film FLM1 or the second reflecting film FLM2 can transmit visible light of about 400 nm to 800 nm. A characteristic RF3 indicates the reflectance of the first reflecting film FLM1 or the second reflecting film FLM2, and according to the characteristic RF3, the first reflecting film FLM1 or the second reflecting film FLM2 can reflect UV light of about 300 nm to 400 nm. Therefore, the UV light of a light amount indicated by area AR3 can be incident on the imaging element 151 or the imaging element 153.

Next, the third prism 33 is exemplified as a visible prism (see the first to sixth configuration examples). However, the third prism 33 is not limited to a visible prism, and may be an IR prism or a UV prism.

The visible prism includes an incidence surface 33a on which light (for example, visible light) transmitted through the second reflecting film FLM2 is incident, and an emission surface 33c from which the transmitted light is emitted. The visible light is incident on the imaging element 152 through the emission surface 33c.

Figure 8D:
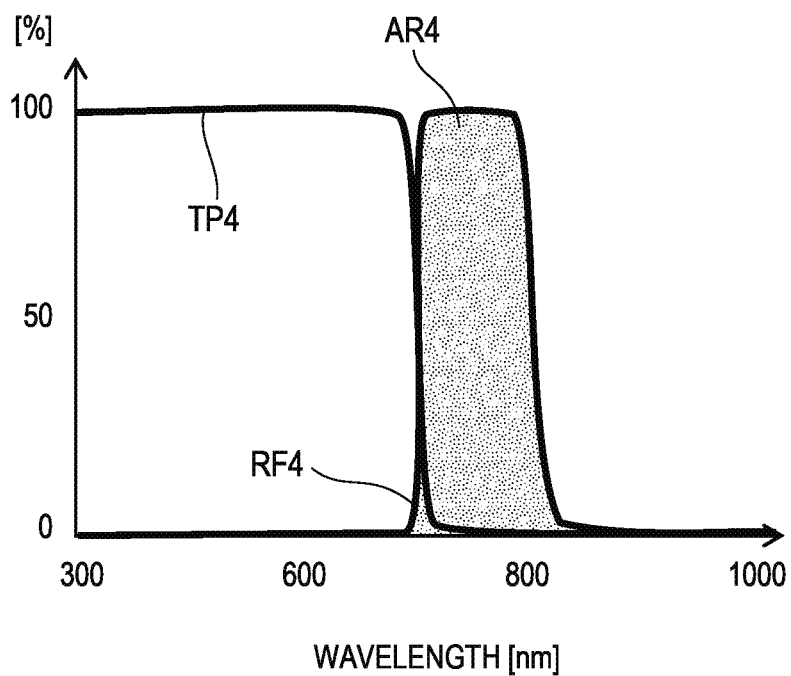
FIG. 8D is a graph illustrating another example of the spectral characteristic of the second reflecting film.
Figure 8E:
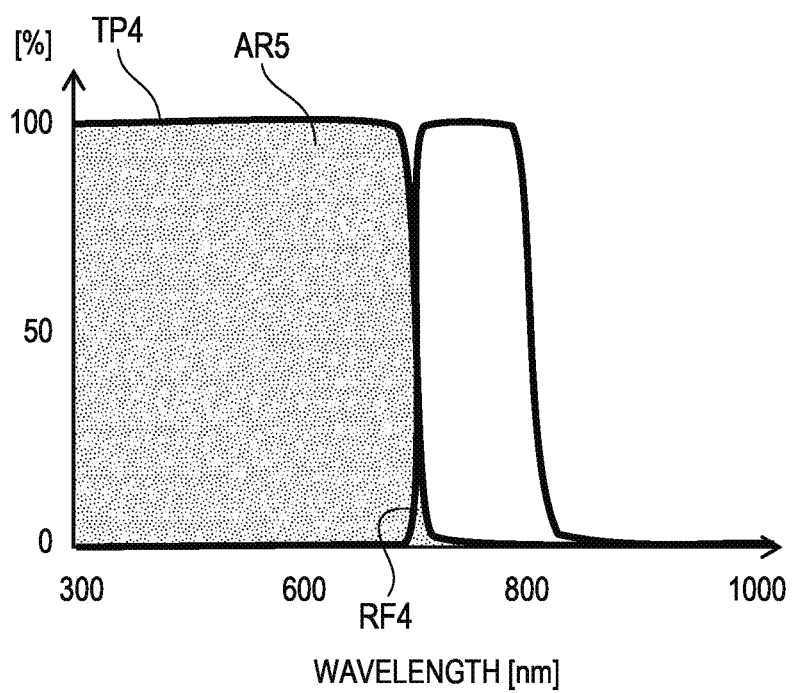
FIG. 8E is a graph illustrating another example of the spectral characteristic of the second reflecting film.

FIGS. 8D and 8E are graphs illustrating another example of the spectral characteristic of the second reflecting film FLM2. In FIGS. 8D and 8E, the horizontal axis represents wavelength [nm: nanometers], and the vertical axis represents reflectance or transmittance. A characteristic TP4 indicates the transmittance (light of 300 nm to 700 nm can transmit) of the second reflecting film FLM2 of the spectral prism 13 according to the third configuration example (see FIG. 3), and a characteristic RF4 indicates the reflectance (light of 700 nm to 800 nm can be reflected) of the second reflecting film FLM2 of the spectral prism 13 according to the third configuration example (see FIG. 3). According to the characteristics TP4 and RF4, the second reflecting film FLM2 of the spectral prism 13 according to the third configuration example (see FIG. 3) can reflect IR light of about 700 nm to 800 nm and transmit UV light of 300 nm to 400 nm and visible light of 400 nm to 700 nm. Therefore, the IR light of a light amount indicated by area AR4 can be incident on the imaging element 151. As illustrated in FIG. 8E, the second reflecting film FLM2 of the spectral prism 13 according to the third configuration example (see FIG. 3) can reflect the IR light of about 700 nm to 800 nm and transmit the UV light of 300 nm to 400 nm and the visible light of 400 nm to 700 nm. The UV light or visible light having a light amount indicated by area AR5 can be incident on the imaging element 152.

Figure 9:
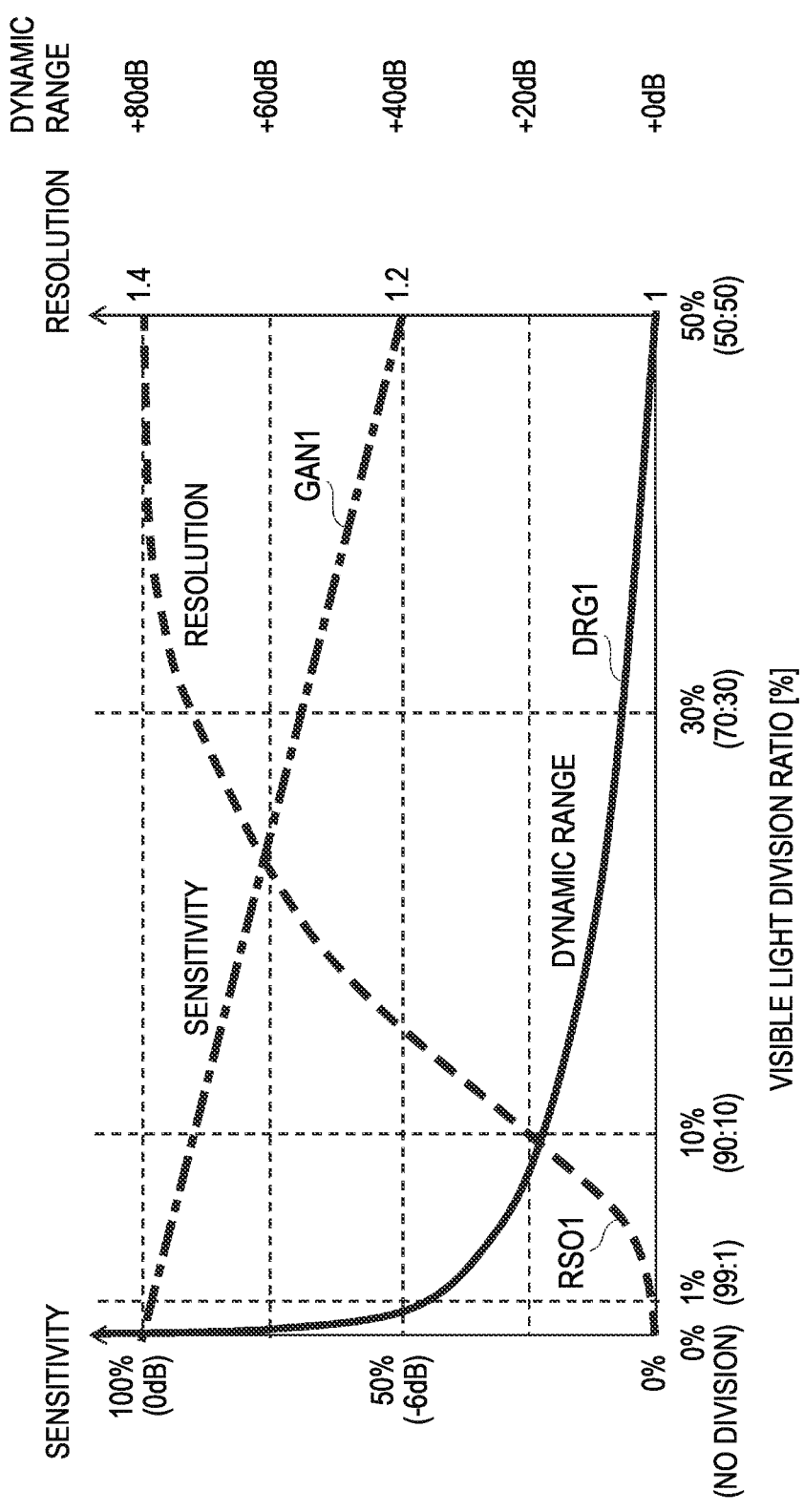
FIG. 9 is a graph illustrating an example of relationships between a visible light division ratio and sensitivity, a dynamic range, and resolution in a case where exposure time of second visible light and that of first visible light are the same.

FIG. 9 is a graph illustrating an example of relationships between a visible light division ratio and sensitivity GAN1, a dynamic range DRG1, and resolution RSO1 in a case where exposure time of the second visible light V2 and exposure time of the first visible light V1 are the same. The horizontal axis in FIG. 9 represents the visible light division ratio, in other words, a proportion at which the light transmitted through the first reflecting film FLM1 (for example, visible light) is reflected by the second reflecting film FLM2 in the first configuration example (see FIG. 1) or the second configuration example (see FIG. 2). For example, when the visible light division ratio is 10% (that is, 90:10), the second reflecting film FLM2 reflects 10% of visible light of the light transmitted through the first reflecting film FLM1, and transmits 90% of the visible light. That is, a light amount of the second visible light V2:a light amount of the first visible light V1 is 90:10. Other visible light division ratios can also be considered in the same manner as the specific example described above. The vertical axis in FIG. 9 represents the sensitivity GAN1, the dynamic range DRG1, and the resolution RSO1 of the wide dynamic range video signal VVD or the high-resolution video signal VVDA generated in the video signal processing units 17 and 17A.

FIG. 9 illustrates an example in which exposure time of each of the imaging elements 152 and 151 is controlled to be the same by an electronic shutter. Therefore, it is considered that the sensitivity GAN1 changes in accordance with a characteristic (for example, a linear function) that: the sensitivity GAN1 increases as the visible light division ratio decreases, is maximum when the visible light division ratio is minimum (for example, the sensitivity GAN1 is most bright at a maximum (100%) when the visible light division ratio is 0%) and is minimum (the darkest at 50%) when the visible light division ratio is 50%. This is because, among brightness of the first visible video signal V1VD based on the first visible light V1 and brightness of the second visible video signal V2VD based on the second visible light V2, the sensitivity is determined by brightness of the brighter second visible light V2.

It is considered that the dynamic range DRG1 changes similarly in accordance with a characteristic that: the dynamic range DRG1 increases as the visible light division ratio decreases in a range larger than 0 (for example, the dynamic range DRG1 is about +80 dB when the visible light division ratio is 0.01%) and is minimum (for example, 0 dB) when the visible light division ratio is 50%. This is because, in the wide dynamic range video signal VVD or the high-resolution video signal VVDA, a difference between a dark portion and a bright portion is more likely to widen as the visible light division ratio decreases.

In contrast, it is considered that the resolution RSO1 changes in accordance with a characteristic that: the resolution RSO1 decreases as the visible light division ratio decreases, is minimum when the visible light division ratio is minimum (for example, the resolution RSO1 is 1 times when the visible light division ratio is 0%), and is maximum (for example, 1.4 times) when the visible light division ratio is 50%. This is because as the visible light division ratio increases, a difference in pixel value between adjacent pixels decreases, and it is more likely to realize high resolution by pixel shift.

Figure 10:
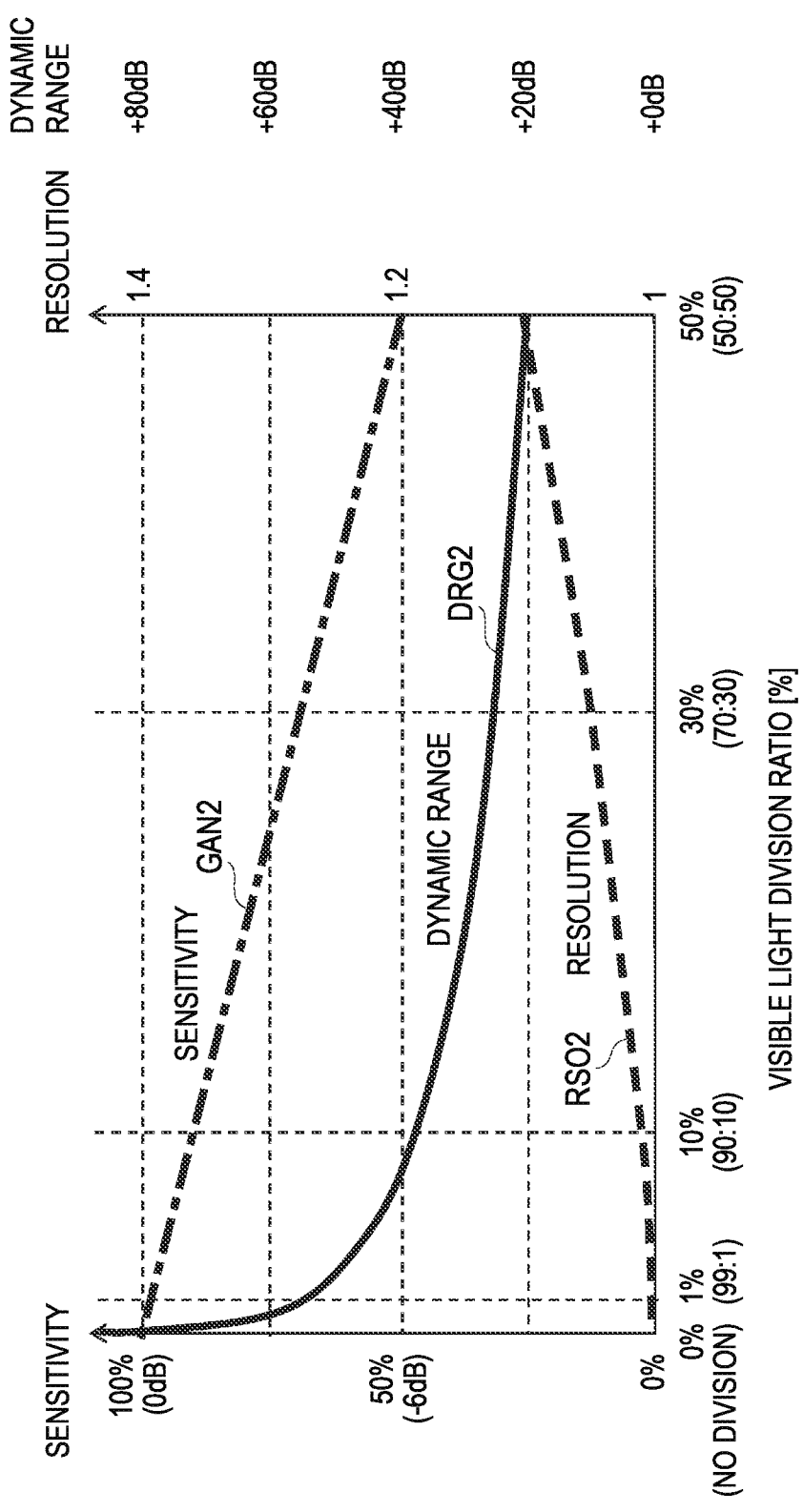
FIG. 10 is a graph illustrating an example of the relationships between the visible light division ratio and the sensitivity, the dynamic range, and the resolution in a case where the exposure time of the second visible light and that of the first visible light are 10:1.

FIG. 10 is a graph illustrating an example of relationships between the visible light division ratio and sensitivity GAN2, a dynamic range DRG2, and resolution RSO2 in a case where exposure time of the second visible light V2 and that of the first visible light V1 are 10:1. The horizontal axis in FIG. 10 represents the visible light division ratio, and is the same as the description of FIG. 9, and thus the description thereof will be omitted. The vertical axis in FIG. 10 represents the sensitivity GAN2, the dynamic range DRG2, and the resolution RSO2 of the wide dynamic range video signal VVD or the high-resolution video signal VVDA generated in the video signal processing units 17 and 17A.

FIG. 10 illustrates an example in which a difference is provided such that exposure time of the imaging element 152 and that of the imaging element 151 are in a ratio of 10:1 by the electronic shutter. Similarly to the sensitivity GAN1 illustrated in FIG. 9, it is considered that the sensitivity GAN2 changes in accordance with a characteristic (for example, a linear function) that: the sensitivity GAN2 increases as the visible light division ratio decreases, is maximum when the visible light division ratio is minimum (for example, the sensitivity GAN2 is most bright at a maximum (100%) when the visible light division ratio is 0%) and is minimum (the darkest at 50%) when the visible light division ratio is 50%. This is because a result obtained by multiplying the ratio 10:1 of the exposure time of the imaging element 152 to the exposure time of the imaging element 151 by a ratio of light amount of the second visible light V2 to a light amount of the first visible light V1 is a ratio of brightness of the second visible video signal V2VD to brightness of the first visible video signal V1VD, and the sensitivity is determined by the brightness of the brighter second visible video signal V2VD.

When a difference is provided such that the exposure time of the imaging element 152 and that of the imaging element 151 are, for example, in a ratio of 10:1 as compared with a case where the exposure time of the imaging element 152 and that of the imaging element 151 are the same, it is considered that, in the wide dynamic range video signal VVD or the high-resolution video signal VVDA, a difference between a bright portion and a dark portion can be more clearly exhibited, and the dynamic range can be further obtained. Accordingly, it is considered that the dynamic range DRG2 changes in accordance with a characteristic that: the dynamic range DRG2 increases as the visible light division ratio decreases in a range larger than 0 (for example, the dynamic range DRG2 is about +80 dB when the visible light division ratio is 0.1%) and is minimum (for example, +20 dB) when the visible light division ratio is 50%. That is, in the example of FIG. 10, even at a minimum value, +20 dB can be obtained.

When a difference is provided such that the exposure time of the imaging element 152 and that of the imaging element 151 are in a ratio of 10:1 by an electronic shutter, for example, when the visible light division ratio is 10% (the second visible light V2:the first visible light V1=90:10), it is considered that a light amount incident on the imaging element 151:a light amount incident on the imaging element 152=100:1. That is, it can be considered that, in the first visible light V1, a dark portion is not substantially reflected, and in the second visible light V2, a bright portion is not substantially reflected, and thus it is substantially difficult to gain resolution when the first visible light V1 and the second visible light V2 are superimposed. Therefore, it is considered that the resolution RSO2 changes in a small value regardless of the visible light division ratio (for example, the resolution RSO2 is approximately 1 times when the visible light division ratio is 0% and approximately 1.1 times even when the visible light division ratio is 50%).

Figure 11:
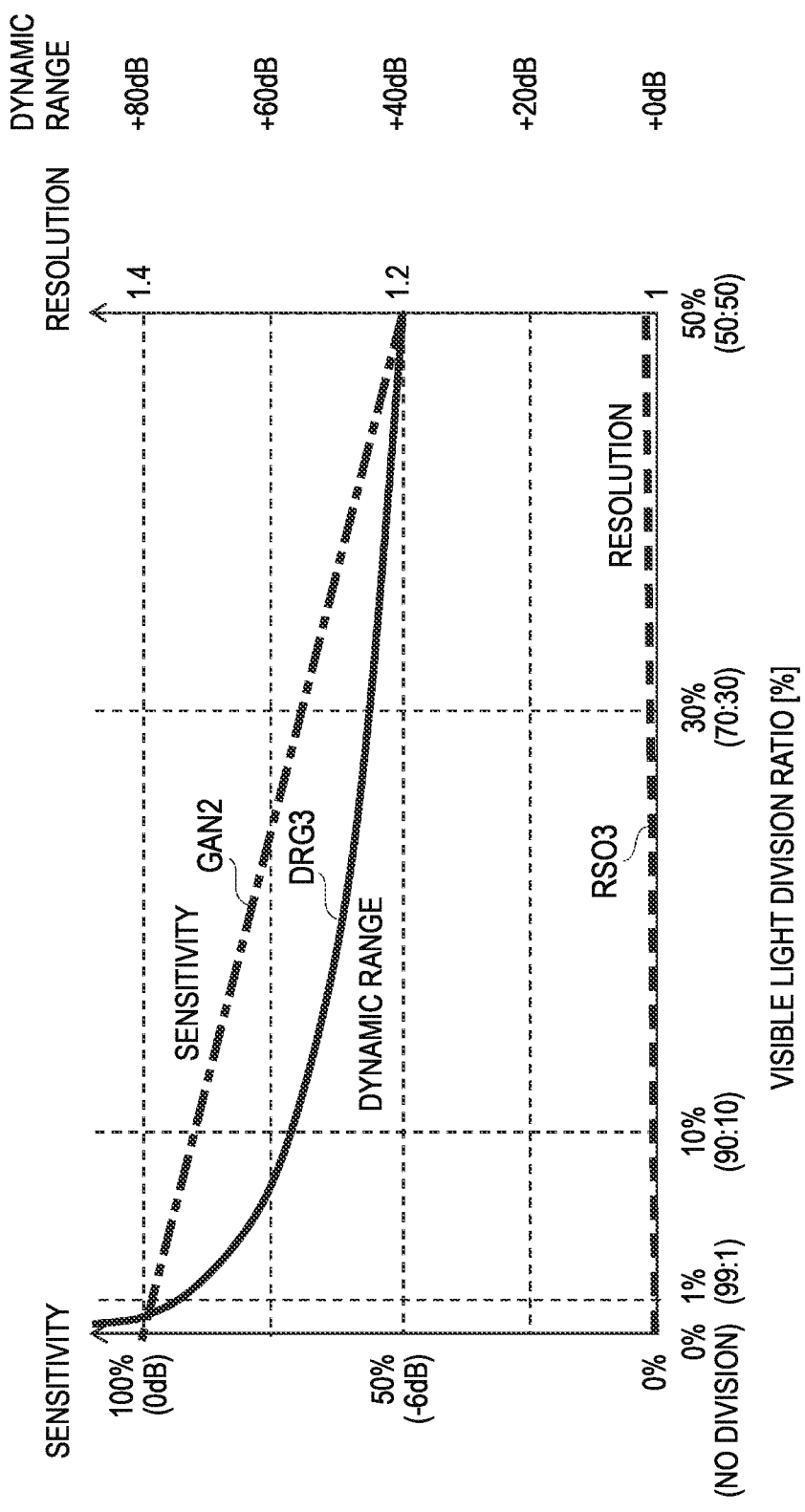
FIG. 11 is a graph illustrating an example of the relationships between the visible light division ratio and the sensitivity, the dynamic range, and the resolution in a case where the exposure time of the second visible light and that of the first visible light are 100:1.

FIG. 11 is a graph illustrating an example of relationships between the visible light division ratio and the sensitivity GAN2, a dynamic range DRG3, and resolution RSO3 in a case where exposure time of the second visible light V2 and that of the first visible light V1 are in a ratio of 100:1. The horizontal axis in FIG. 11 represents the visible light division ratio, and is the same as the description of FIG. 9, and thus the description thereof will be omitted. The vertical axis in FIG. 11 represents the sensitivity GAN2, the dynamic range DRG3, and the resolution RSO3 of the wide dynamic range video signal VVD or the high-resolution video signal VVDA generated in the video signal processing units 17 and 17A.

FIG. 11 illustrates an example in which a difference is provided such that exposure time of the imaging element 152 and that of the imaging element 151 are in a ratio of 100:1 by an electronic shutter. Similarly to the sensitivity GAN2 illustrated in FIG. 10, it is considered that the sensitivity GAN2 changes in accordance with a characteristic (for example, a linear function) that: the sensitivity GAN2 increases as the visible light division ratio decreases, is maximum when the visible light division ratio is minimum (for example, the sensitivity GAN2 is most bright at a maximum (100%) when the visible light division ratio is 0%) and is minimum (the darkest at 50%) when the visible light division ratio is 50%. This is because a result obtained by multiplying the ratio 100:1 of the exposure time of the imaging element 152 to the exposure time of the imaging element 151 by a ratio of light amount of the second visible light V2 to a light amount of the first visible light V1 is a ratio of brightness of the second visible video signal V2VD to brightness of the first visible video signal V1VD, and the sensitivity is determined by the brightness of the brighter second visible video signal V2VD.

When a difference is provided such that the exposure time of the imaging element 152 and that of the imaging element 151 are, for example, in a ratio of 100:1 as compared with a case where the exposure time of the imaging element 152 and that of the imaging element 151 are the same, it is considered that, in the wide dynamic range video signal VVD or the high-resolution video signal VVDA, a difference between a bright portion and a dark portion can be furthermore clearly exhibited, and a larger dynamic range can be obtained. Accordingly, it is considered that the dynamic range DRG3 changes in accordance with a characteristic that: the dynamic range DRG3 increases as the visible light division ratio decreases in a range larger than 0 (for example, the dynamic range DRG3 is about +80 dB when the visible light division ratio is 1%) and is minimum (for example, +40 dB) when the visible light division ratio is 50%. That is, in the example of FIG. 11, even at a minimum value, +40 dB can be obtained.

When a difference is provided such that the exposure time of the imaging element 152 and that of the imaging element 151 are in a ratio of 100:1 by an electronic shutter, for example, when the visible light division ratio is 10% (the second visible light V2:the first visible light V1=90:10), it is considered that a light amount incident on the imaging element 152:a light amount incident on the imaging element 151=1000:1. That is, it can be considered that, the second visible light V2 is too bright and a dark portion is not reflected, and the first visible light V1 is too dark and a bright portion is not reflected, and thus it is almost difficult to obtain the resolution when the second visible light V2 and the first visible light V1 are superimposed as compared with the example of FIG. 10. Therefore, it is considered that the resolution RSO3 changes in a small value regardless of the visible light division ratio (for example, the resolution RSO3 is approximately 1 times when the visible light division ratio is 0% and approximately 1.02 times even when the visible light division ratio is 50%).

Figure 12:
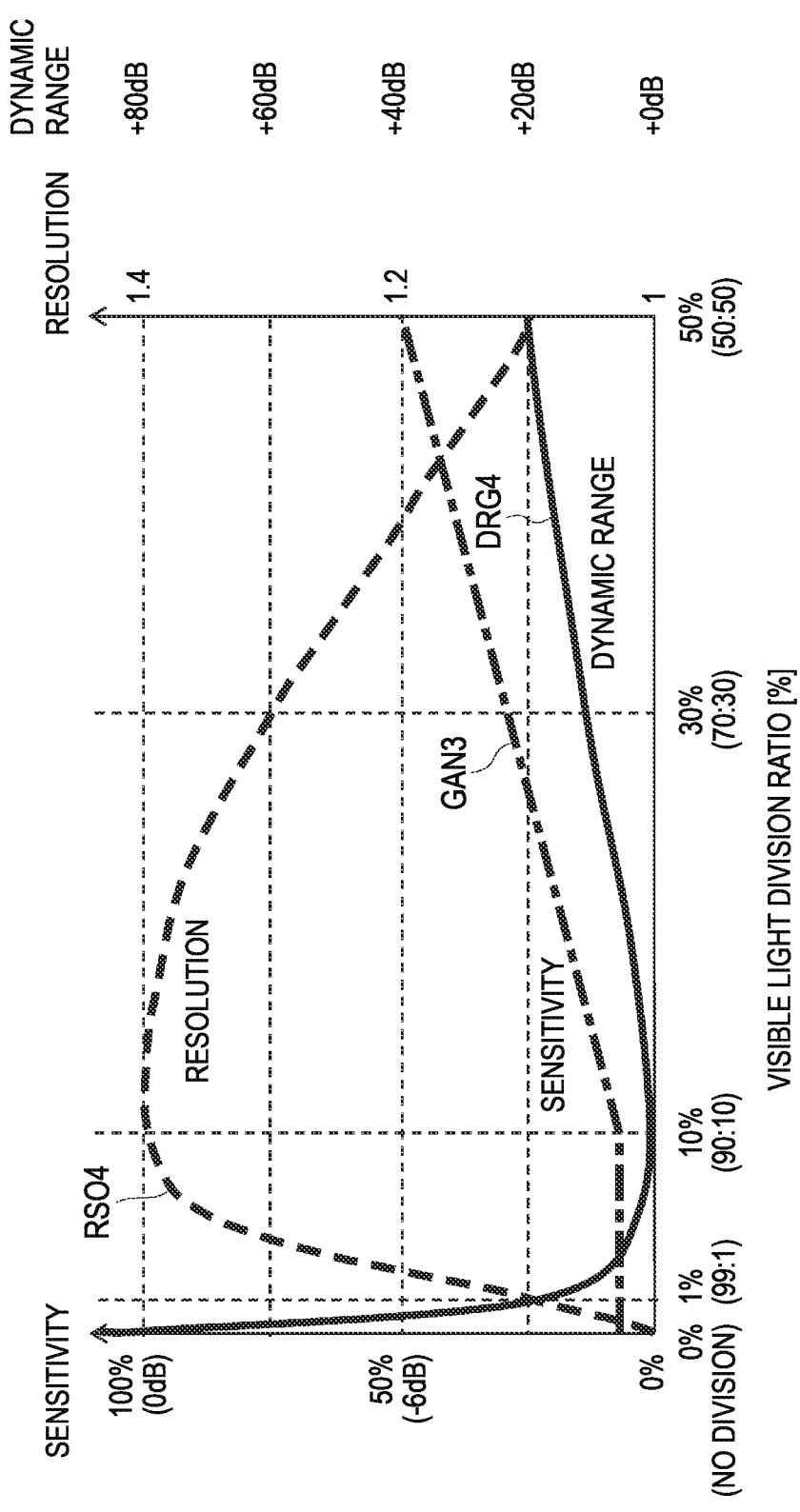
FIG. 12 is a graph illustrating an example of the relationships between the visible light division ratio and the sensitivity, the dynamic range, and the resolution in a case where the exposure time of the second visible light and that of the first visible light are 1:10.

FIG. 12 is a graph illustrating an example of relationships between the visible light division ratio and sensitivity GAN3, a dynamic range DRG4, and resolution RSO4 in a case where exposure time of the second visible light V2 and that of the first visible light V1 are in a ratio of 1:10. The horizontal axis in FIG. 12 represents the visible light division ratio, and is the same as the description of FIG. 9, and thus the description thereof will be omitted. The vertical axis in FIG. 12 represents the sensitivity GAN3, the dynamic range DRG4, and the resolution RSO4 of the wide dynamic range video signal VVD or the high-resolution video signal VVDA generated in the video signal processing units 17 and 17A.

FIG. 12 illustrates an example in which a difference is provided such that exposure time of the imaging element 152 and that of the imaging element 151 are in a ratio of 1:10 by an electronic shutter. In contrast with the example of FIG. 10, when a difference is provided such that the exposure time of the imaging element 152 and that of the imaging element 151 are, for example, in a ratio of 1:10, for example, when the visible light division ratio is 10% (the second visible light V2:the first visible light V1=90:10), it is considered that a light amount incident on the imaging element 152 and a light amount incident on the imaging element 151 are substantially equal to each other by cancellation of the visible light division ratio and an exposure time ratio. Therefore, the sensitivity GAN3 changes in accordance with a characteristic that: the sensitivity GAN3 is substantially constant as a minimum when the visible light division ratio ranges from 0% to 10% (in other words, when light amounts incident on the respective imaging elements 152 and 151 do not change much), and monotonically increases in a linear function when the visible light division ratio is greater than 10% and no more than 50%. For example, the brightness is maximum (50%, that is, −6 dB) when the visible light division ratio is 50%. This is because a result obtained by multiplying the ratio 1:10 of the exposure time of the imaging element 152 to the exposure time of the imaging element 151 by a ratio of light amount of the second visible light V2 to a light amount of the first visible light V1 is a ratio of brightness of the second visible video signal V2VD to brightness of the first visible video signal V1VD, and the sensitivity is determined by the brightness of the brighter visible video signal.

When a difference is provided such that the exposure time of the imaging element 152 and that of the imaging element 151 are, for example, in a ratio of 1:10 as compared with a case where the exposure time of the imaging element 152 and that of the imaging element 151 are the same, it is considered that, in the wide dynamic range video signal VVD or the high-resolution video signal VVDA, it is easy to obtain a difference in brightness when the visible light division ratio decreases in a range greater than 0%, but a difference between a bright portion and a dark portion is unlikely to be exhibited as the visible light division ratio increases and it is difficult to obtain the dynamic range. Therefore, the dynamic range DRG4 increases as the visible light division ratio decreases in a range greater than 0% (for example, about +80 dB when the visible light division ratio is 0.001%), but when the visible light division ratio is 10%, the ratio 1:10 of the exposure time of the imaging element 152 to the exposure time of the imaging element 151 is cancelled, the brightness of the second visible video signal V2VD and the brightness of the first visible video signal V1VD are substantially equal to each other, and the dynamic range DRG4 is minimum. When the visible light division ratio exceeds 10%, a difference in brightness between the second visible video signal V2VD and the first visible video signal V1VD occurs again, so that the dynamic range DRG4 increases. When the visible light division ratio is 50%, a ratio of the brightness of the second visible video signal V2VD to the brightness of the first visible video signal V1VD is 1:10 obtained by multiplying the ratio 1:10 of the exposure time of the imaging element 152 to the exposure time of the imaging element 151, and accordingly the dynamic range is +20 dB.

When a difference is provided such that the exposure time of the imaging element 152 and that of the imaging element 151 are in a ratio of 1:10 by an electronic shutter, for example, when the visible light division ratio is 10% (the second visible light V2:the first visible light V1=90:10), it is considered that a light amount incident on the imaging element 151 and a light amount incident on the imaging element 152 are substantially equal (see the above description). That is, it is considered that the resolution RSO4 changes in accordance with a characteristic that: the resolution RSO4 is maximized since the first visible video signal V1VD based on the first visible light V1 and the second visible video signal V2VD based on the second visible light V2 have the same brightness when cancellation of the visible light division ratio and the exposure time ratio (1:10) occurs (for example, when the visible light division ratio is 10%), and decreases from a maximum value when the visible light division ratio is one that makes cancellation less likely to occur.

Figure 13:
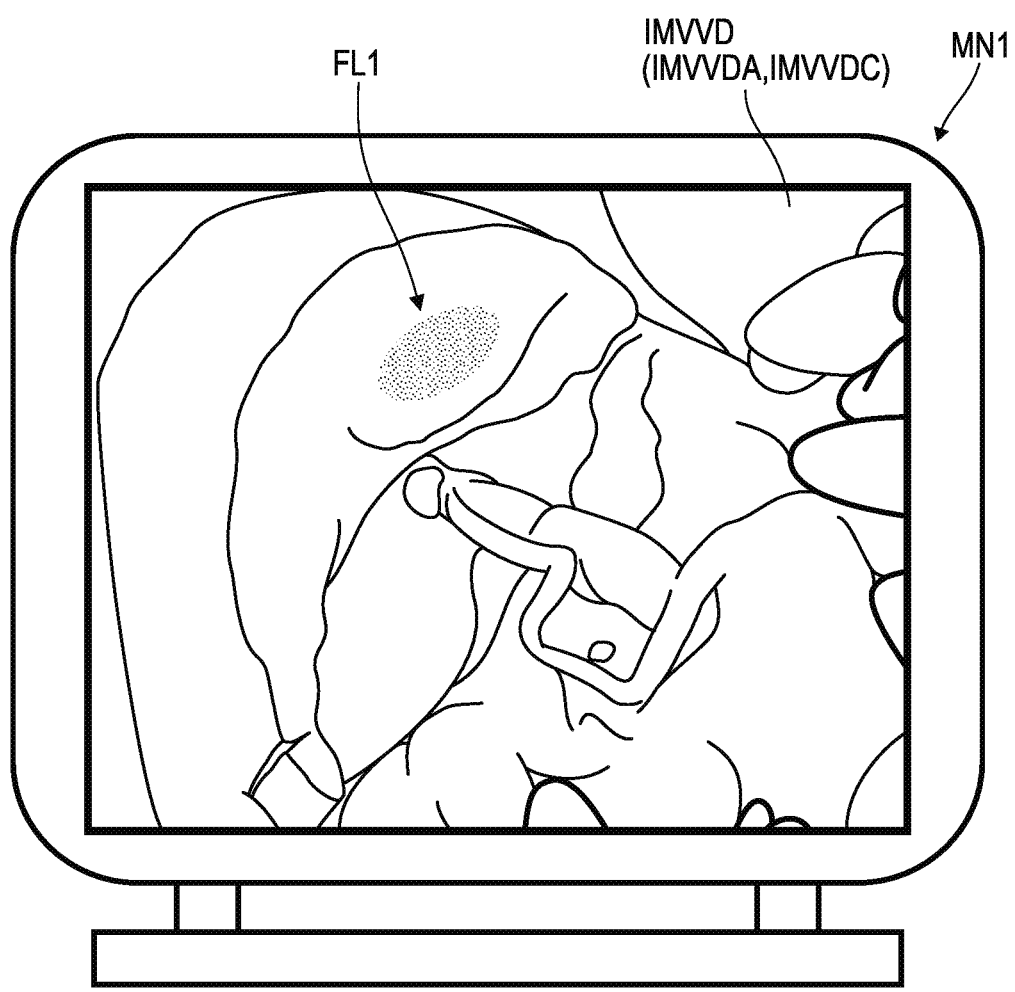
FIG. 13 is a diagram illustrating a display example on a monitor of a visible/IR combined video signal generated by the three-plate camera according to the first embodiment.

FIG. 13 is a diagram illustrating a display example on the monitor MN1 of visible/IR combined video signals IMVVD, IMVVDA, and IMVVDC generated by the three-plate cameras 1, 1A, and 1C according to the first embodiment. The visible/IR combined video signals IMVVD, IMVVDA, and IMVVDC illustrated in FIG. 13 are generated based on imaging at an observation part (for example, the liver and the periphery of the pancreas) of a patient that is a subject, and are displayed on the monitor MN1. In FIG. 13, a fluorescent reagent of the ICG administered to an affected part in the patient's body in advance before surgery or examination emits light, and the visible/IR combined video signals IMVVD, IMVVDA, and IMVVDC indicate a location thereof (for example, an affected part FL1). As described above, the three-plate cameras 1, 1A, and 1C can generate, for example, high-quality visible/IR combined video signals IMVVD, IMVVDA, and IMVVDC that can allows understanding of details of the observation part by a user such as a doctor at the time of surgery or examination, and display the generated visible/IR combined video signals IMVVD, IMVVDA, and IMVVDC on the monitor MN1. Such a display example is not limited to the three-plate camera according to the first embodiment, and a visible/IR combined video signal generated by a four-plate camera according to a second embodiment described later may also be displayed on the monitor MN1 in the same manner.

Figure 14:
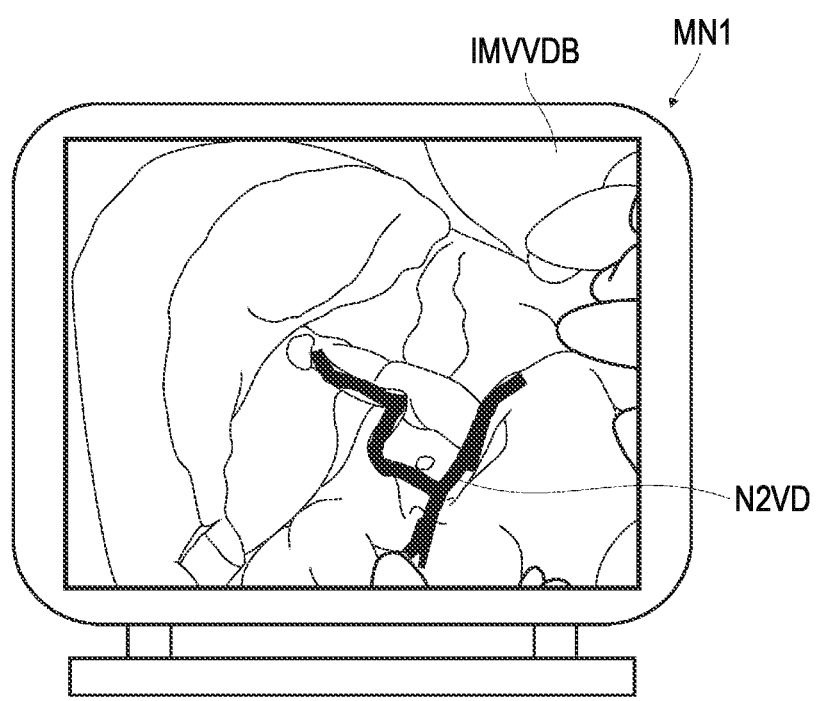
FIG. 14 is a diagram illustrating another display example on the monitor of the visible/IR combined video signal generated by the three-plate camera according to the first embodiment.

FIG. 14 is a diagram illustrating a display example on the monitor MN1 of visible/IR combined video signals IMVVDB generated by a three-plate camera 1B according to the first embodiment. The visible/IR combined video signal IMVVDB illustrated in FIG. 14 is generated based on imaging at an observation part (for example, the liver and the periphery of the pancreas) of a patient that is a subject, and is displayed on the monitor MN1. Since the first IR video signal N2VD and the second IR video signal N3VD are combined in the visible/IR combined video signal IMVVDB, which are based on imaging of the first IR light N2 and the second IR light N3 that are separated (dispersed) into two types of wavelength bands, it is possible to allow a user, such as a doctor, to understand in detail whether there is a vein or an artery in the observation part. For example, it is known that, in a wavelength band of 700 nm to 800 nm, an absorption coefficient of venous blood is higher than that of arterial blood, and conversely, in a wavelength band of 800 nm to 900 nm, the absorption coefficient of arterial blood is higher than that of venous blood, and the absorption coefficient of arterial blood and the absorption coefficient of venous blood are reversed with the vicinity of 800 nm as a boundary. Thus, the three-plate camera 1B can identify whether the blood transferred to the visible/IR combined video signal IMVVDB is arterial blood or venous blood depending on a ratio of an intensity of the first IR light N2 having a wavelength of 700 nm to 800 nm to an intensity of the second IR light N3 having a wavelength of 800 nm to 900 nm.

In FIG. 14, for example, it is indicated, by the first IR video signal N2VD, that an artery exists. As described above, for example, the three-plate camera 1B can generate a high-quality visible/IR combined video signal IMVVDB that allows a user such as a doctor to understand details of an observation part (in particular, presence or absence of a vein and an artery) at the time of surgery or examination, and display the visible/IR combined video signal IMVVDB on the monitor MN1. Such a display example is not limited to the three-plate camera according to the first embodiment, and a visible/IR combined video signal generated by a four-plate camera according to a second embodiment described later may also be displayed on the monitor MN1 in the same manner.

As described above, the three-plate camera according to the first embodiment includes a IR prism that causes an IR image sensor to receive incident IR light of light from an observation part, a visible prism that causes a visible image sensor to receive incident visible light of the light from the observation part, and a specific prism that causes a specific image sensor to receive incident light of a specific wavelength band of the light from the observation part. The three-plate camera includes a video signal processing unit that generates an IR video signal, a visible video signal, and a specific video signal of the observation part based on respective imaging outputs of the IR image sensor, the visible image sensor, and the specific image sensor, combines the IR video signal, the visible video signal, and the specific video signal, and outputs a combined signal to the monitor MN1.

Accordingly, with the spectral prism 13, the three-plate camera can separate (disperse) IR light, which is specialized in a specific wavelength band (for example, 800 nm or more), that is, a fluorescence region of a fluorescent reagent, out of light from the observation part (for example, an affected part) to which the fluorescent reagent (for example, ICG) is administered into a subject such as a patient in advance at the time of surgery or examination. Therefore, the three-plate camera can generate and output a clearer fluorescent image of the observation part to which the fluorescent reagent is administered and a color video by the visible light, and thus can support easy understanding of the affected part for a doctor or the like.

The light of a specific wavelength band is the second visible light V2 having the same wavelength band as the visible light (for example, the first visible light V1). The video signal processing unit 17 combines a visible video signal (for example, the first visible video signal V1VD) and a second visible video signal V2VD that is based on the second visible light V2 to generate a wide dynamic range video signal VVD, and combines the wide dynamic range video signal VVD and an IR video signal N1VD. Accordingly, the three-plate camera (for example, the three-plate camera 1) can display a visible/IR combined video signal IMVVD obtained by combining the IR video signal N1VD and the wide dynamic range video signal VVD on the monitor MN1, and thus can present a video allowing to identify in detail a clear surgical field and a location of the affected part to a user such as a doctor and can appropriately support a medical practice for the user.

The light of a specific wavelength band is the second visible light V2 having the same wavelength band as the visible light (for example, the first visible light V1). The video signal processing unit 17 combines the visible video signal (for example, the first visible video signal V1VD) and the second visible video signal V2VD that is based on the second visible light V2 to generate a high-resolution video signal VVDA, and combines the high-resolution video signal VVDA and the IR video signal N1VD. Accordingly, the three-plate type camera (for example, the three-plate camera 1A) can display a visible/IR combined image signal IMVVDA obtained by combining the IR video signal N1VD and the high-resolution video signal VVDA on the monitor MN1, and thus can present a video allowing to identify in detail a structure and a location of an affected part having a complicated shape to a user such as a doctor and can support appropriately a medical practice for the user.

Further, the light of a specific wavelength band is the second IR light N3 having a near infrared wavelength band different from the IR light (for example, the first IR light N2). For example, a wavelength band of the first IR light N2 is 800 nm to 1000 nm, and a wavelength band of the second IR light N3 is 700 nm to 800 nm. The video signal processing unit 17 combines an IR video signal (for example, the first IR video signal N2VD), a visible video signal V3VD, and a second IR video signal N3VD that is based on the second IR light N3. Accordingly, the three-plate camera (for example, the three-plate camera 1B) superimposes the first IR video signal N2VD and the second IR video signal N3VD that are based on imaging of a plurality of beams of IR light having different wavelength bands to be imaged, and thus can display an IR video signal showing a more precise condition of the affected part by reaction (light emission) of the fluorescent reagent on the monitor MN1 together with a color video of a surgical field, and can appropriately support a medical practice of a user such as a doctor.

Further, the light of a specific wavelength band is the UV light U1 having a wavelength band shorter than that of the visible light V3. The video signal processing unit 17 combines the IR video signal N1VD, the visible video signal V3VD, and the UV video signal U1VD that is based on the UV light U1. Accordingly, the three-plate camera (for example, the three-plate camera 1C) superimposes the UV video signal U1VD, the visible video signal V3VD, and the IR video signal N1VD that are based on imaging of a plurality of beams of light having different wavelength bands imaged by the image sensors of three channels, and thus can display on the monitor MN1 not only a color video of a surgical field and the IR video signal showing a condition of an affected part based on reaction (light emission) of the fluorescent reagent, but also the UV video signal showing a condition of the affected part obtained by imaging of the UV light, and can appropriately support a medical practice for a user such as a doctor.

Further, the three-plate camera according to the first embodiment includes a first visible prism that causes a first visible image sensor to receive incident first visible light of light from an observation part, a second visible prism that causes a second visible image sensor to receive incident second visible light of the light from the observation part, and a specific prism that causes a specific image sensor to receive incident light of a specific wavelength band of the light from the observation part. The three-plate camera includes a video signal processing unit that generates a first visible video signal, a second visible video signal, and a specific video signal of the observation part based on respective imaging outputs of the first visible image sensor, the second visible image sensor, and the specific image sensor, combines the first visible video signal, the second visible video signal, and the specific video signal, and outputs a combined signal to the monitor MN1.

Accordingly, by superimposing a plurality of beams of visible light having different light amounts (brightness) at the time of surgery or examination, the three-plate camera not only can display the wide dynamic range video signal VVDD having a wider dynamic range than a single color video on the monitor MN1, but also can display a captured video based on one more channel of imaging light. Therefore, the three-plate camera can present, to a user such as a doctor, a video that allows identification of a clear situation of a surgical field by darkly or brightly projecting the surgical field, and can appropriately support a medical practice for the user.

Further, the light of a specific wavelength band light is the third visible light V4 having the same wavelength band as the first visible light V1 and the second visible light V2. The video signal processing unit 17D combines the first visible video signal V1VD, the second visible video signal V2VD, and a third visible video signal that is based on the third visible light to generate a wide dynamic range video signal. Accordingly, since the three-plate camera 1D superimposes the visible video signals of three channels having different light amounts, it is possible to display on the monitor MN1 a video having a wider dynamic range as compared with a single color video. Thus it is possible to present, to a user such as a doctor, a video that makes it easy to understand a more clear and detailed surgical field, and it is possible to appropriately support a medical practice for the user.

In addition, each of the second visible prism and the specific prism is disposed farther from an observation part side than the first visible prism. Accordingly, the reflecting film (for example, the second reflecting film FLM2) disposed in the vicinity of a bonding surface between the first visible prism and the second visible prism may be configured to have a characteristic for reflecting visible light having the same wavelength band as visible light incident on the first visible prism, and thus manufacturing accuracy of the reflecting film can be improved as compared with a case where the reflecting film has a characteristic for reflecting IR light having a wavelength band different from the visible light.

Second Embodiment

In the first embodiment, a three-plate camera equipped with the spectral prism 13 formed by bonding three prisms is described. In a second embodiment, an example of a four-plate camera equipped with a spectral prism 14 formed by bonding four prisms will be described.

Seventh Configuration Example

In a seventh configuration example, it is assumed that a light amount of the first visible light V1 incident on the imaging element 151 and a light amount of the second visible light V2 incident on the imaging element 152 are different from each other, and IR light and UV light are respectively imaged.

Figure 15:
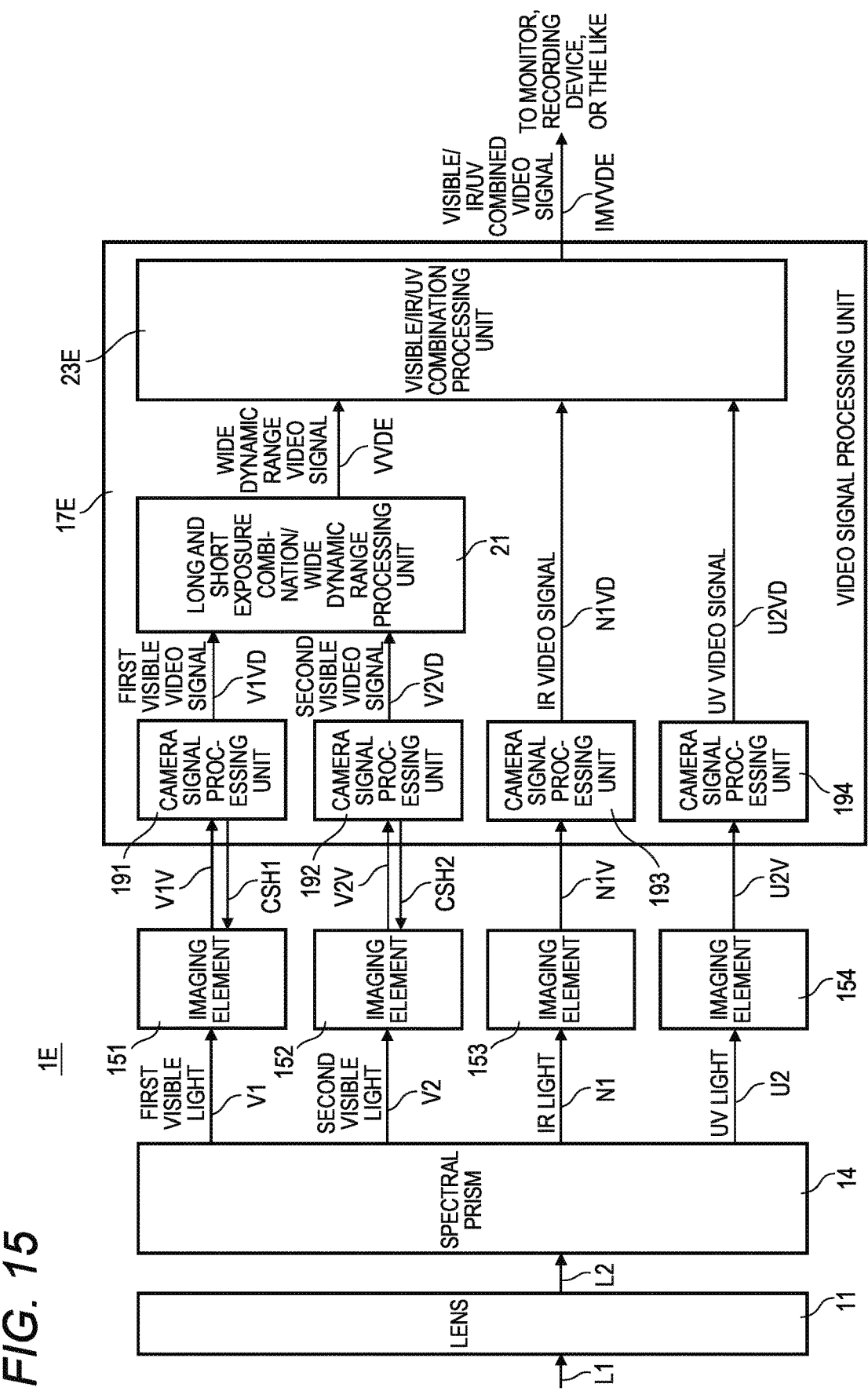
FIG. 15 is a block diagram illustrating an internal configuration example of a four-plate camera according to a seventh configuration example.

FIG. 15 is a block diagram illustrating an internal configuration example of a four-plate camera 1E according to the seventh configuration example. The four-plate camera 1E includes the lens 11, the spectral prism 14, imaging elements 151, 152, 153, and 154, and a video signal processing unit 17E. The video signal processing unit 17E includes camera signal processing units 191, 192, 193, and 194, the long and short exposure combination/wide dynamic range processing unit 21, and a visible/IR/UV combination processing unit 23E. In the description of FIG. 15, the same components as those in FIG. 1 are denoted by the same reference signs, and a description thereof will be simplified or omitted, and different contents will be described. In the description of a configuration in which the four-plate camera according to the second embodiment described below is capable of imaging at least two channels of visible light (specifically, the seventh configuration example, a ninth configuration example, a tenth configuration example, and an eleventh configuration example), the long and short exposure combination/wide dynamic range processing unit 21 and the like may not only perform processing for having a color video having a wide dynamic range described in the first configuration example, but also perform the high-resolution processing (see the above description) performed by the pixel-shift combination/high-resolution processing unit 25 in the second configuration example. Further, in the description of the configuration in which the four-plate camera according to the second embodiment described below is capable of imaging at least two channels of visible light (see the above description), the pixel-shift combination/high-resolution processing unit 25 may be used in place of the long and short exposure combination/wide dynamic range processing unit 21 and the like.

The fourth-plate camera (see FIGS. 15 and 18) according to the second embodiment is used in, for example, a medical observation system that irradiates a fluorescent reagent (for example, indocyanine green that is abbreviated as "ICG" in the following description) administered in advance to an observation part (for example, an affected part) in a subject such as a patient with excitation light of a predetermined wavelength band (for example, 760 nm to 800 nm) at the time of surgery or examination, and that images the observation part emitting fluorescence at a long wavelength side (for example, 820 nm to 860 nm) based on the excitation light. An image (for example, a video of an observation part) imaged by the four-plate camera is displayed by a monitor MN1 (see FIG. 13), and supports execution of a medical practice by a user such as a doctor. Although an example in which the spectral prism 14 is used in, for example, the above-described medical observation system is described, the use thereof is not limited to medical applications and may be industrial applications.

The spectral prism 14 as an example of an optical component receives the light L2 from the observation part, and disperses the light L2 into the first visible light V1, the second visible light V2, the IR light N1, and UV light U2. The spectral prism 14 has a configuration in which a first prism 41 (for example, an IR prism), a second prism 42 (for example, a UV prism), a third prism 43 (for example, a visible prism), and a fourth prism 44 (for example, a visible prism) are bonded in order (see FIG. 19). The first visible light V1 is incident on the imaging element 151 that is disposed so as to face the third prism 43 (for example, a visible prism). The second visible light V2 is incident on the imaging element 152 that is disposed so as to face the fourth prism 44 (for example, a visible prism). The IR light N1 is incident on the imaging element 153 that is disposed so as to face the first prism 41 (for example, an IR prism). The UV light U2 is incident on the imaging element 154 that is disposed so as to face the second prism 42 (for example, a UV prism). A detailed example of a structure of the spectral prism 14 will be described later with reference to FIG. 20.

The imaging element 151 as an example of a visible image sensor includes, for example, a CCD or CMOS in which a plurality of pixels suitable for imaging of visible light are arranged, and an exposure control circuit (not illustrated) using an electronic shutter. The imaging element 151 is disposed so as to face the third prism 43 (for example, a visible prism) (see FIG. 20). The imaging element 151 performs imaging based on the first visible light V1 incident over first exposure time that is determined by the exposure control circuit based on the exposure control signal CSH1 from the camera signal processing unit 191. The imaging element 151 generates the video signal V1V of the observation part by imaging, and outputs the video signal V1V to the video signal processing unit 17E.

The imaging element 152 as an example of a second specific image sensor includes, for example, a CCD or CMOS in which a plurality of pixels suitable for imaging of visible light are arranged, and an exposure control circuit (not illustrated) using an electronic shutter. The imaging element 152 is disposed so as to face the fourth prism 44 (for example, a visible prism) (see FIG. 20). The imaging element 152 performs imaging based on the second visible light V2 incident over second exposure time that is determined by the exposure control circuit based on an exposure control signal CSH2 from the camera signal processing unit 192. The imaging element 152 generates the video signal V2V of the observation part by imaging, and outputs the video signal V2V to the video signal processing unit 17E.

The imaging element 153 as an example of an IR image sensor includes, for example, a CCD or a CMOS in which a plurality of pixels suitable for imaging of IR light are arranged. The imaging element 153 is disposed so as to face the first prism 41 (for example, an IR prism) (see FIG. 20). The imaging element 153 performs imaging based on the incident IR light N1. The imaging element 153 generates the video signal N1V of the observation part by imaging, and outputs the video signal N1V to the video signal processing unit 17E.

The imaging element 154 as an example of a first specific image sensor includes, for example, a CCD or a CMOS in which a plurality of pixels suitable for imaging of UV light are arranged. The imaging element 154 is disposed so as to face the second prism 42 (for example, a UV prism) (see FIG. 20). The imaging element 154 performs imaging based on the incident UV light U2. The imaging element 154 generates a video signal U2V of the observation part by imaging, and outputs the video signal U2V to the video signal processing unit 17E.

The video signal processing unit 17E is configured with a processor such as a DSP or an FPGA, for example. Each of the camera signal processing units 191 to 194, the long and short exposure combination/wide dynamic range processing unit 21, and the visible/IR combination processing unit 23E is implemented by the processor described above.

The camera signal processing unit 191 performs various types of camera signal processing using the video signal V1V from the imaging element 151 to generate the first visible video signal V1VD of the observation part, and outputs the first visible video signal V1VD to the long and short exposure combination/wide dynamic range processing unit 21. In addition, the camera signal processing unit 191 generates the exposure control signal CSH1 for determining first exposure time of the imaging element 151 and outputs the exposure control signal CSH1 to the imaging element 151. The imaging element 151 controls the first exposure time of the first visible light V1 based on the exposure control signal CSH1.

The camera signal processing unit 192 performs various types of camera signal processing using the video signal V2V from the imaging element 152 to generate the second visible video signal V2VD of the observation part, and outputs the second visible video signal V2VD to the long and short exposure combination/wide dynamic range processing unit 21. Here, in the seventh configuration example, a light amount of the first visible light V1 incident on the imaging element 151 is different from a light amount of the second visible light V2 incident on the imaging element 152. Therefore, the first visible video signal V1VD from the camera signal processing unit 191 and the second visible video signal V2VD from the camera signal processing unit 192 are different in brightness (sensitivity). In addition, the camera signal processing unit 192 generates the exposure control signal CSH2 for determining second exposure time of the imaging element 152 and outputs the exposure control signal CSH2 to the imaging element 152. The imaging element 152 controls the second exposure time of the second visible light V2 based on the exposure control signal CSH2. The first exposure time and the second exposure time may be the same or different.

The camera signal processing unit 193 performs various types of camera signal processing using the video signal N1V from the imaging element 153 to generate the IR video signal N1VD of the observation part, and outputs the IR video signal N1VD to the visible/IR/UV combination processing unit 23E.

The camera signal processing unit 194 performs various types of camera signal processing using the video signal U2V from the imaging element 154 to generate a UV video signal U2VD of the observation part, and outputs the UV video signal U2VD to the visible/IR/UV combination processing unit 23E.

The visible/IR/UV combination processing unit 23E receives a wide dynamic range video signal VVDE from the long and short exposure combination/wide dynamic range processing unit 21, the IR video signal N1VD from the camera signal processing unit 193, and the UV video signal U2VD from the camera signal processing unit 194 and combines the signals by superimposition, and generates a visible/IR/UV combined video signal IMVVDE. The visible/IR/UV combination processing unit 23E may output the visible/IR/UV combined video signal IMVVDE to the monitor MN1 or transmit the visible/IR/UV combined video signal IMVVDE to a recording device (not illustrated) for accumulation.

Eighth Configuration Example

In an eighth configuration example, it is assumed that imaging is performed by using an imaging element capable of imaging two different wavelength bands among wavelength bands of near-infrared (IR) light using two channels (for example, imaging elements 153 and 154 illustrated in FIG. 16), and visible light and UV light are imaged, respectively.

Figure 16:
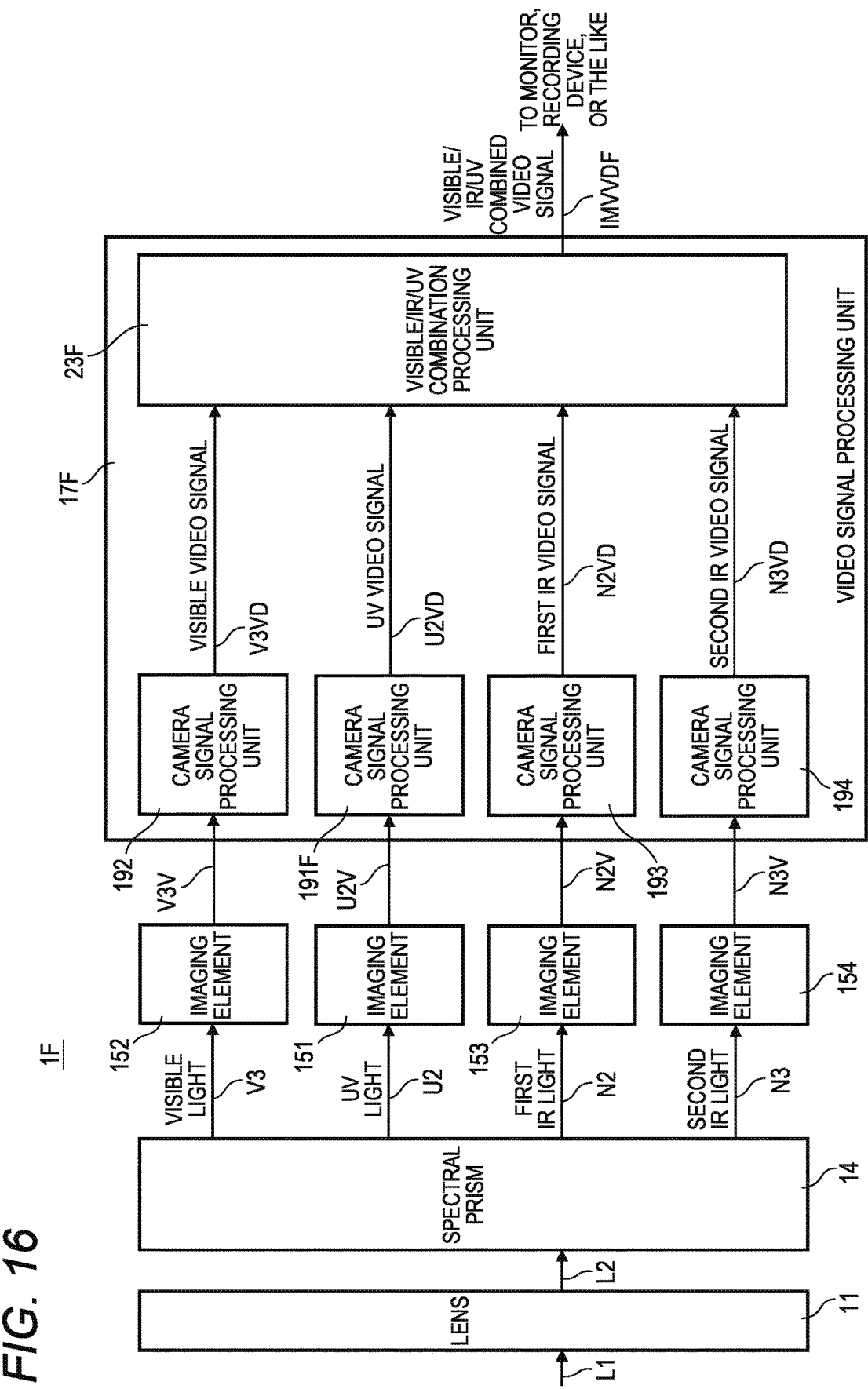
FIG. 16 is a block diagram illustrating an internal configuration example of a four-plate camera according to an eighth configuration example.

FIG. 16 is a block diagram illustrating an internal configuration example of a four-plate camera 1F according to the eighth configuration example. The four-plate camera 1F includes the lens 11, the spectral prism 14, the imaging elements 151, 152, 153, and 154, and a video signal processing unit 17F. The video signal processing unit 17F includes camera signal processing units 191F, 192, 193, and 194, and a visible/IR/UV combination processing unit 23F. In the description of FIG. 16, the same components as those in FIG. 15 are denoted by the same reference signs, and a description thereof will be simplified or omitted, and different contents will be described.

The four-plate camera according to the second embodiment (see FIGS. 16 and 17) is used in, for example, a medical observation system that irradiates a plurality of types of fluorescent reagents (for example, ICG) administered in advance to observation parts (for example, an affected part) in a subject such as a patient with excitation light of a predetermined wavelength band at the time of surgery or examination, and that images the observation parts emitting fluorescence at a long wavelength side (for example, 700 nm to 800 nm and 800 nm to 900 nm) based on the excitation light. An image (for example, a video of an observation part) imaged by the four-plate camera 1F is displayed by the monitor MN1 (see FIG. 14), and supports execution of a medical practice by a user such as a doctor.

The spectral prism 14 as an example of an optical component receives the light L2 from the observation part and disperses the light L2 into the visible light V3, the UV light U2, the first IR light N2, and the second IR light N3. The spectral prism 14 has a configuration in which the first prism 41 (for example, an IR prism), the second prism 42 (for example, an IR prism), the third prism 43 (for example, a UV prism), and a fourth prism 44 (for example, a visible prism) are bonded in order (see FIG. 20). The visible light V3 is incident on the imaging element 152 that is disposed so as to face the fourth prism 44 (for example, a visible prism). The UV light U2 is incident on the imaging element 151 that is disposed so as to face the third prism 43 (for example, a UV prism). The first IR light N2 is incident on the imaging element 153 that is disposed so as to face the first prism 41 (for example, an IR prism). The second IR light N3 is incident on the imaging element 154 that is disposed so as to face the second prism 42 (for example, an IR prism). A detailed example of a structure of the spectral prism 14 will be described later with reference to FIG. 20.

The imaging element 151 as an example of a second specific image sensor includes, for example, a CCD or a CMOS in which a plurality of pixels suitable for imaging of UV light are arranged. The imaging element 151 is disposed so as to face the third prism 43 (see FIG. 20). The imaging element 151 generates a video signal U2V of the observation part by imaging, and outputs the video signal U2V to the video signal processing unit 17F.

The video signal processing unit 17F is configured with a processor such as a DSP or an FPGA, for example. Each of the camera signal processing units 191F, 192 to 194, and the visible/IR/UV combination processing unit 23F is implemented by the processor described above.

The camera signal processing unit 191F performs various types of camera signal processing using the video signal U2V from the imaging element 151 to generate the UV video signal U2VD of the observation part, and outputs the UV video signal U2VD to the visible/IR/UV combination processing unit 23F.

The visible/IR/UV combination processing unit 23F receives the UV video signal U2VD from the camera signal processing unit 191F, the visible video signal V3VD from the camera signal processing unit 192, the first IR video signal N2VD from the camera signal processing unit 193, and the second IR video signal N3VD from the camera signal processing unit 194 and combines the signals by superimposition, and generates a visible/IR/UV combined video signal IMVVDF. The visible/IR/UV combination processing unit 23F may output the visible/IR/UV combined video signal IMVVDF to the monitor MN1 or transmit the visible/IR/UV combined video signal IMVVDF to a recording device (not illustrated) for accumulation.

Ninth Configuration Example

In a ninth configuration example, it is assumed that a light amount of the first visible light V1 incident on the imaging element 151 and a light amount of the second visible light V2 incident on the imaging element 152 are different from each other, and that imaging is performed by using an imaging element capable of imaging two different wavelength bands among wavelength bands of the near-infrared (IR) light using two channels (for example, the imaging elements 153 and 154 illustrated in FIG. 16).

Figure 17:
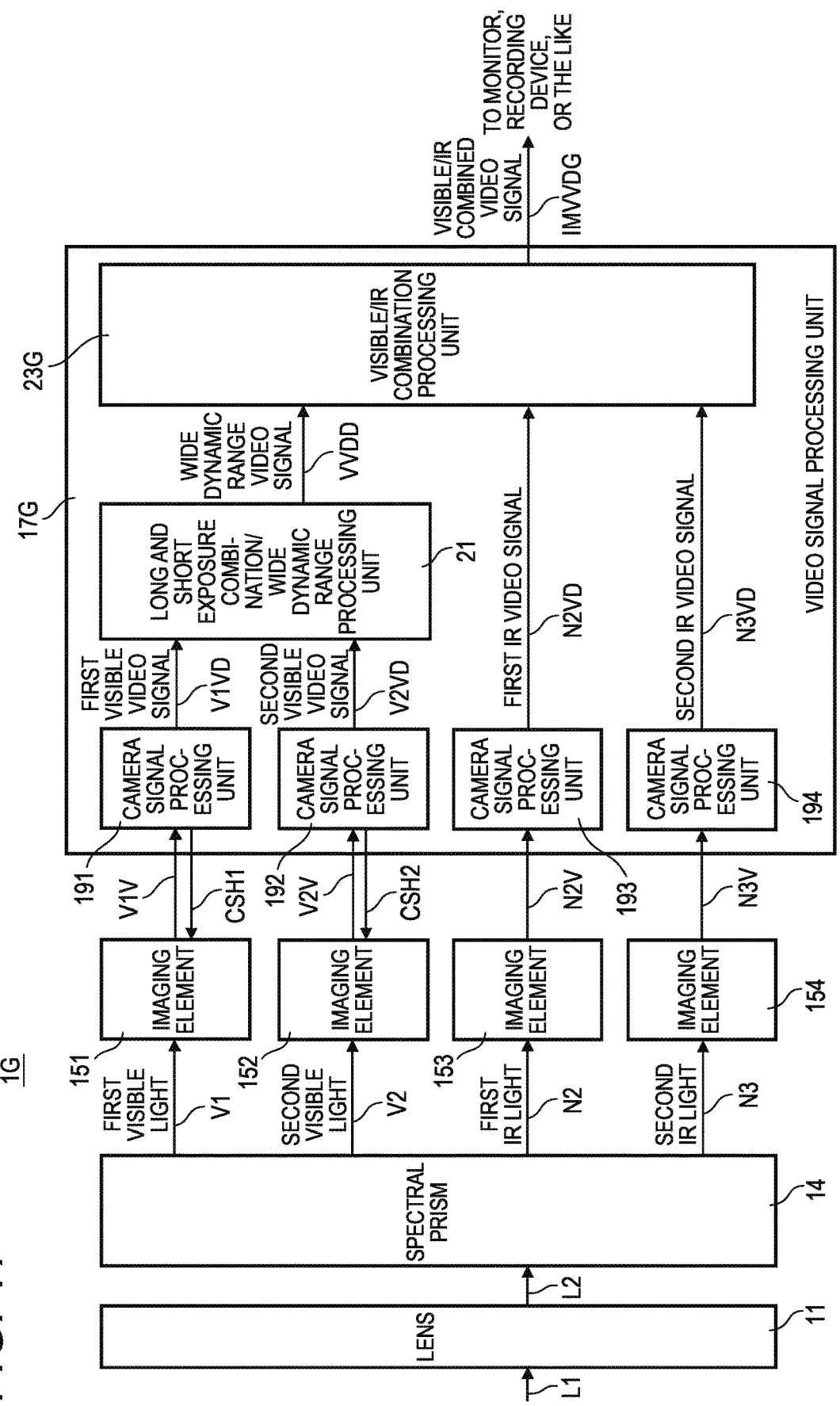
FIG. 17 is a block diagram illustrating an internal configuration example of a four-plate camera according to a ninth configuration example.

FIG. 17 is a block diagram illustrating an internal configuration example of a four-plate camera 1G according to the ninth configuration example. The four-plate camera 1G includes the lens 11, the spectral prism 14, the imaging elements 151, 152, 153, and 154, and a video signal processing unit 17G. The video signal processing unit 17G includes camera signal processing units 191, 192, 193, and 194G and a visible/IR combination processing unit 23G. In the description of FIG. 17, the same components as those in FIG. 15 or 16 are denoted by the same reference signs, and a description thereof will be simplified or omitted, and different contents will be described.

The spectral prism 14 as an example of an optical component receives the light L2 from the observation part, and disperses the light L2 into the first visible light V1, the second visible light V2, the first IR light N2, and the second IR light N3. The spectral prism 14 has a configuration in which the first prism 41 (for example, an IR prism), the second prism 42 (for example, an IR prism), the third prism 43 (for example, a visible prism), and the fourth prism 44 (for example, a visible prism) are bonded in order (see FIG. 20). The first visible light V1 is incident on the imaging element 151 that is disposed so as to face the third prism 43. The second visible light V2 is incident on the imaging element 152 that is disposed so as to face the fourth prism 44. The first IR light N2 is incident on the imaging element 153 that is disposed so as to face the first prism 41. The second IR light N3 is incident on the imaging element 154 that is disposed so as to face the second prism 42. A detailed example of a structure of the spectral prism 14 will be described later with reference to FIG. 20.

The imaging element 154 as an example of a first specific image sensor includes, for example, a CCD or a CMOS in which a plurality of pixels suitable for imaging of IR light are arranged. The imaging element 154 is disposed so as to face the second prism 42 (see FIG. 20). The imaging element 154 performs imaging based on the incident second IR light N3. The imaging element 154 generates the video signal N3V of the observation part by imaging, and outputs the video signal N3V to the video signal processing unit 17G.

The video signal processing unit 17G is configured with a processor such as a DSP or an FPGA, for example. Each of the camera signal processing units 191 to 193 and 194G and the visible/IR combination processing unit 23G is implemented by the processor described above.

The camera signal processing unit 194G performs various types of camera signal processing using the video signal N3V from the imaging element 154 to generate the second IR video signal N3VD of the observation part, and outputs the second IR video signal N3VD to the visible/IR combination processing unit 23G.

The visible/IR combination processing unit 23G receives the first visible video signal V1VD from the camera signal processing unit 191, the second visible video signal V2VD from the camera signal processing unit 192, the first IR video signal N2VD from the camera signal processing unit 193, and the second IR video signal N3VD from the camera signal processing unit 194G and combines the signals by superimposition, and generates a visible/IR combined video signal IMVVDG. The visible/IR combination processing unit 23G may output the visible/IR combined video signal IMVVDG to the monitor MN1 or transmit the visible/IR combined video signal IMVVDG to a recording device (not illustration) for accumulation.

Tenth Configuration Example

Figure 18:
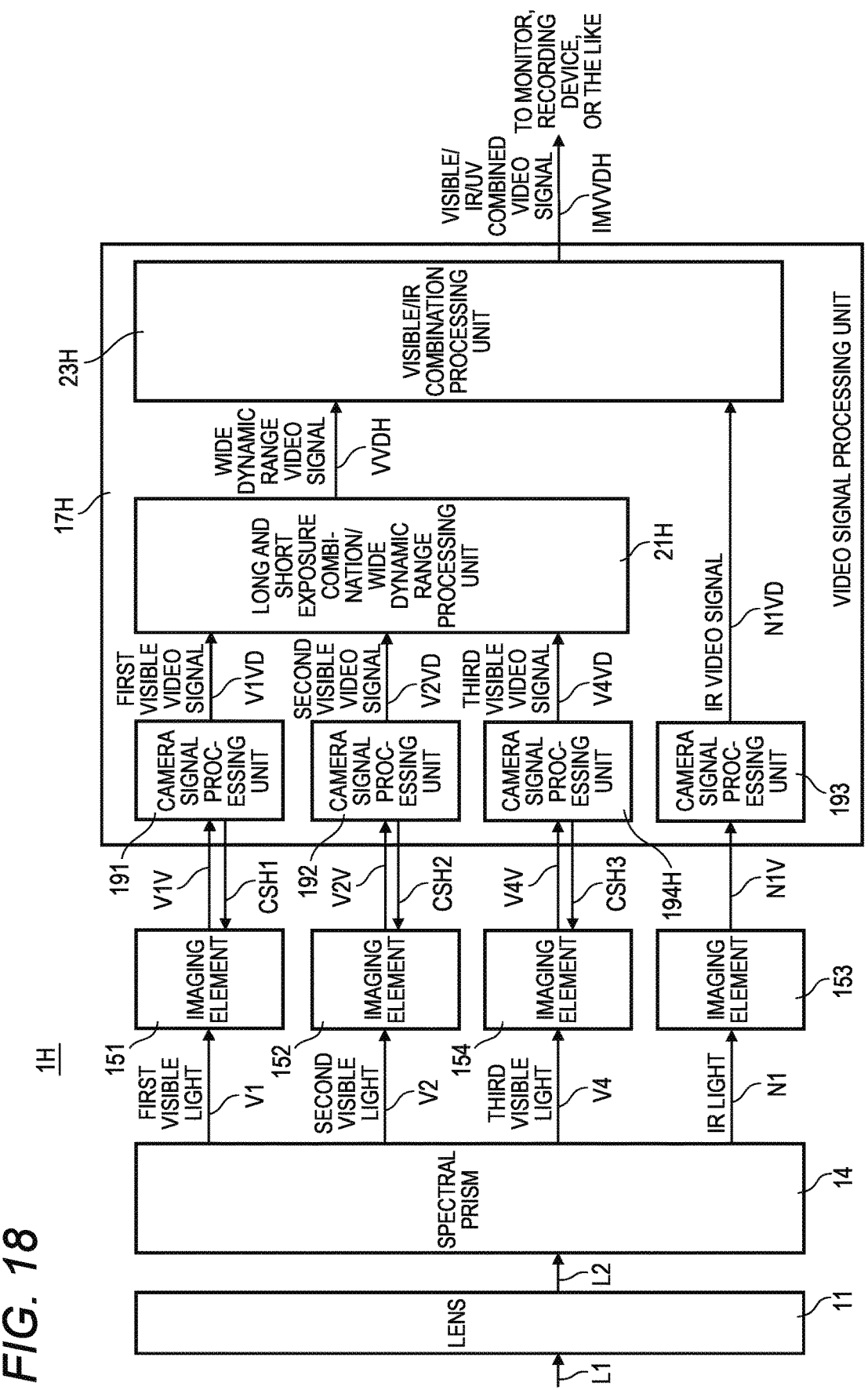
FIG. 18 is a block diagram illustrating an internal configuration example of a four-plate camera according to a tenth configuration example.

In a tenth configuration example, it is assumed that imaging is performed by using an imaging element capable of imaging a wavelength band of visible light using three channels (for example, imaging elements 151, 152, and 153 illustrated in FIG. 18), and light amounts of visible light incident on respective imaging elements are different from each other. Accordingly, it is possible to generate a video signal that allows identifying in detail a condition of a surrounding portion of a surgical field or the like according to a color video having an observation part or a high dynamic range in a periphery thereof.

FIG. 18 is a block diagram illustrating an internal configuration example of a four-plate camera 1H according to the tenth configuration example. The four-plate camera 1H includes the lens 11, the spectral prism 14, the imaging elements 151, 152, 153, and 154, and a video signal processing unit 17H. The video signal processing unit 17H includes camera signal processing units 191, 192, 193, and 194H, and a visible/IR combination processing unit 23H. In the description of FIG. 18, the same components as those in FIGS. 15 to 17 are denoted by the same reference signs, and a description thereof will be simplified or omitted, and different contents will be described.

The spectral prism 14 as an example of an optical component receives the light L2 from the observation part, and disperses the light L2 into the first visible light V1, the second visible light V2, the third visible light V4, and the IR light N1. The spectral prism 14 has a configuration in which the first prism 41 (for example, an IR prism), the second prism 42 (for example, a visible prism), the third prism 43 (for example, a visible prism), and the fourth prism 44 (for example, a visible prism) are bonded in order (see FIG. 20). The first visible light V1 is incident on the imaging element 151 that is disposed so as to face the third prism 43. The second visible light V2 is incident on the imaging element 152 that is disposed so as to face the fourth prism 44. The IR light N1 is incident on the imaging element 153 that is disposed so as to face the first prism 41. The third visible light V4 is incident on the imaging element 154 that is disposed so as to face the second prism 42. A detailed example of a structure of the spectral prism 14 will be described later with reference to FIG. 20.

The imaging element 154 as an example of a second specific image sensor includes, for example, a CCD or CMOS in which a plurality of pixels suitable for imaging of visible light are arranged, and an exposure control circuit (not illustrated) using an electronic shutter. The imaging element 154 is disposed so as to face the second prism 42 (see FIG. 20). The imaging element 154 performs imaging based on the third visible light V4 incident over third exposure time that is determined by the exposure control circuit based on the exposure control signal CSH3 from the camera signal processing unit 194H. The imaging element 154 generates the video signal V4V of the observation part by imaging, and outputs the video signal V4V to the video signal processing unit 17H.

The camera signal processing unit 194H performs various types of camera signal processing using the video signal V4V from the imaging element 154 to generate the third visible video signal V4VD of the observation part, and outputs the third visible video signal V4VD to a long and short exposure combination/wide dynamic range processing unit 21H. In addition, the camera signal processing unit 194H generates the exposure control signal CSH3 for determining the third exposure time of the imaging element 154, and outputs the exposure control signal CSH3 to the imaging element 154. The imaging element 154 controls the third exposure time of the third visible light V4 based on the exposure control signal CSH3.

The long and short exposure combination/wide dynamic range processing unit 21H receives three video signals having different brightness (sensitivity) (specifically, the first visible video signal V1VD from the camera signal processing unit 191, the second visible video signal V2VD from the camera signal processing unit 192, and the third visible video signal V4VD from the camera signal processing unit 194H) and combines the three video signals by superimposition, and generates a wide dynamic range video signal VVDH. That is, by combining the first visible video signal V1VD, the second visible video signal V2VD, and the third visual video signal V4VD having different brightness (sensitivity), the long and short exposure combination/wide dynamic range processing unit 21H can generate the wide dynamic range video signal VVDH having a wider dynamic range than the first visible video signal V1VD, the second visible video signal V2VD, or the third visible video signal V4VD. The long and short exposure combination/wide dynamic range processing unit 21H outputs the wide dynamic range video signal VVDH to the visible/IR combination processing unit 23H.

The visible/IR combination processing unit 23H receives the wide dynamic range video signal VVDH from the long and short exposure combination/wide dynamic range processing unit 21H and the IR video signal N1VD from the camera signal processing unit 193, and combines the two signals by superimposition, and generates a visible/IR combined video signal IMVVDH. The visible/IR combination processing unit 23H may output the visible/IR combined video signal IMVVDH to the monitor MN1 or transmit the visible/IR combined video signal IMVVDH to a recording device (not illustration) for accumulation.

FIG. 19 is a table illustrating a combination example of configuration examples of the fourth-plate camera according to the second embodiment. In FIG. 19, the seventh configuration example is described with reference to FIG. 15, the eighth configuration example is described with reference to FIG. 16, the ninth configuration example is described with reference to FIG. 17, and the tenth configuration example is described with reference to FIG. 18. As the four-plate camera according to the second embodiment, as a modification of the tenth configuration example (that is, an eleventh configuration example), light incident on the first prism 41 may be UV light. That is, in the description of FIG. 18, the "IR light" may be replaced with "UV light", the "video signal N1V" may be replaced with "video signal U1V", and the "IR video signal N1VD" may be replaced with "UV video signal U1VD".

Figure 20:
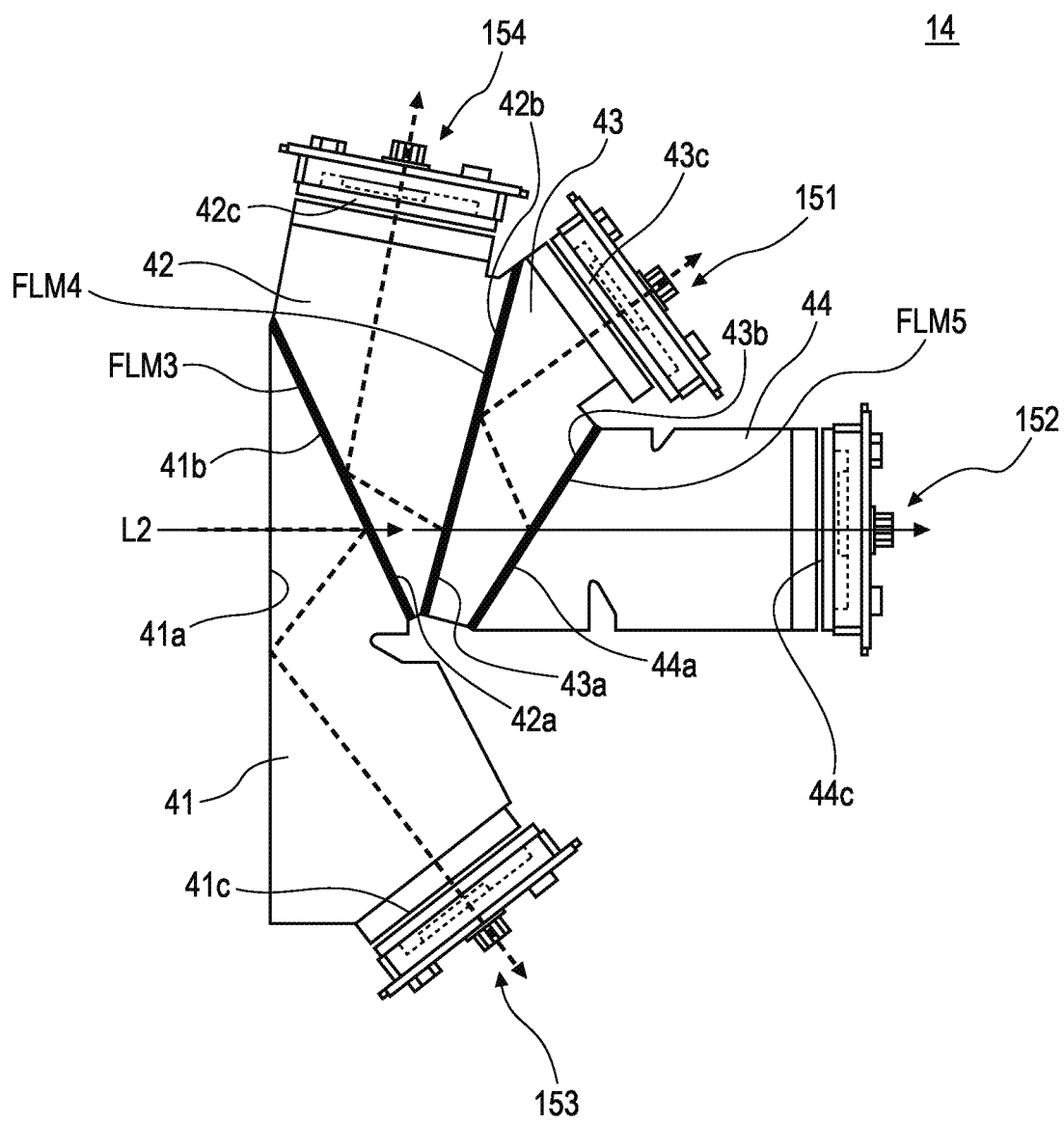
FIG. 20 is a diagram illustrating an example of a structure of a spectral prism according to the second embodiment.

FIG. 20 is a diagram illustrating an example of the structure of the spectral prism 14 according to the second embodiment. As described above, the spectral prism 14 has a configuration in which the first prism 41, the second prism 42, the third prism 43, and the fourth prism 44 are bonded in order. The first prism 41, the second prism 42, the third prism 43, and the fourth prism 44 are assembled in order in the optical axis direction of the light L2 concentrated by the lens 11. Here, the optical axis direction is a direction in which the light L2 is incident perpendicularly to an incidence surface 41a of the first prism 41. In the seventh configuration example to the eleventh configuration example described above, the roles (in other words, functions and applications) of the first prism 41, the second prism 42, the third prism 43, and the fourth prism 44 may be the same or different.

First, the first prism 41 is exemplified as an IR prism (see the seventh to tenth configuration examples). However, the first prism 41 is not limited to the IR prism, and may be a visible prism or a UV prism (see the eleventh configuration example).

The IR prism includes the incidence surface 41a on which the light L2 is incident, a reflecting surface 41b on which a first reflecting film FLM3 (for example, a dichroic mirror) for reflecting IR light in the light L2 is formed, and an emission surface 41c from which the IR light is emitted. The first reflecting film FLM3 is formed on the reflecting surface 41b by vapor deposition or the like, and reflects IR light (for example, IR light in a wavelength band of 800 nm or more) in the light L2, and transmits light (for example, UV light of about 300 nm to 400 nm or visible light of about 400 nm to 800 nm) that is not the IR light in the light L2 (see FIG. 8A). The IR light is totally reflected by the incidence surface 41a after being reflected by the reflection surface 41b, and is incident on the imaging element 153 through the emission surface 41c. In this way, since the IR prism is disposed as the first prism 41, the IR component light in the light L2 from an observation part is imaged on the most target-facing side (that is, the observation part side) of the spectral prism 14. Compared with a case where the IR component light is imaged at a rear stage side (that is, a base end side) of the spectral prism 14, attenuation of a light amount due to reflection or the like does not occur, and a condition of an affected part based on fluorescence emission of a fluorescent reagent can be more clearly identified.

Next, the second prism 42 is exemplified as a UV prism (see the seventh configuration example). However, the second prism 42 is not limited to a UV prism, and may be an IR prism (see the eighth and ninth configuration examples) or a visible prism (see the tenth and eleventh configuration examples).

The UV prism includes an incidence surface 42a on which light transmitted through the first reflecting film FLM3 is incident, a reflecting surface 42b on which a second reflecting film FLM4 (for example, a beam splitter) for reflecting UV light having a wavelength band of 300 nm to 400 nm of the transmitted light is formed, and an emission surface 42c from which visible light having other wavelength bands (for example, 400 m to 800 nm) is emitted. The second reflecting film FLM4 is formed on the reflecting surface 42b by vapor deposition or the like, reflects UV light of light incident on the incidence surface 42a, and transmits the remaining visible light (see FIG. 8C). The UV light is totally reflected by the incidence surface 42a after being reflected by the reflecting surface 42b, and is incident on the imaging element 154 through the emission surface 42c.

Next, the third prism 43 is exemplified as a visible prism (see the seventh, ninth, tenth, and eleventh configuration examples). However, the third prism 43 is not limited to a visible prism, and may be an IR prism or a UV prism (see the eighth configuration example).

The visible prism includes an incidence surface 43a on which light transmitted through the second reflecting film FLM4 is incident, a reflecting surface 43b on which a third reflecting film FLM5 (for example, a beam splitter) for reflecting a light amount of a part of the transmitted light is formed, and an emission surface 43c from which reflected visible light of the light amount of the part of the transmitted light is emitted. The third reflecting film FLM5 is formed on the reflecting surface 43b by vapor deposition or the like, reflects visible light having a light amount of a part of the visible light incident on the incidence surface 43a (for example, about 20% of the light incident on the incidence surface 43a), and transmits visible light having the remaining light amount (for example, about 80% of the light incident on the incidence surface 43a) (see FIG. 8B). The part of visible light is totally reflected by the incidence surface 43a after being reflected by the reflecting surface 43b, and is incident on the imaging element 151 through the emission surface 43c. The proportion of the visible light reflected by the third reflecting film FLM5 is not limited to 20%, and may be, for example, in a range of about 1% to 30%.

Next, the fourth prism 44 is exemplified as a visible prism (see the seventh to the eleventh configuration examples). However, the fourth prism 44 is not limited to a visible prism, and may be an IR prism or a UV prism.

The visible prism includes an incidence surface 44a on which light (for example, visible light) transmitted through the third reflecting film FLM5 is incident, and an emission surface 44c from which the transmitted light is emitted. The visible light is incident on the imaging element 152 through the emission surface 44c.

As described above, the four-plate camera according to the second embodiment includes an IR prism that causes an IR image sensor to receive incident IR light of light from an observation part, a visible prism that causes a visible image sensor to receive incident visible light of the light from the observation part, a first specific prism that causes a first specific image sensor to receive incident light of a first specific wavelength band of the light from the observation part, and a second specific prism that causes a second specific image sensor to receive incident light of a second specific wavelength band of the light from the observation part. The fourth-plate camera includes a video signal processing unit that generates an IR video signal, a visible video signal, a first specific video signal, and a second specific video signal of the observation part based on respective imaging outputs of the IR image sensor, the visible image sensor, the first specific image sensor, and the second specific image sensor, combines the IR video signal, the visible video signal, the first specific video signal, and the second specific video signal, and outputs a combined signal to the monitor MN1.

Accordingly, with the spectral prism 14, the four-plate camera can separate (disperse) IR light, which is specialized in a specific wavelength band (for example, 800 nm or more), that is, a fluorescence region of a fluorescent reagent, out of light from the observation part (for example, an affected part) to which the fluorescent reagent (for example, ICG) is administered into a subject such as a patient in advance at the time of surgery or examination. Therefore, the four-plate camera can generate and output a clearer fluorescent image of the observation part to which the fluorescent reagent is administered and a color video by the visible light, and thus can support easy understanding of the affected part for a doctor or the like.

Further, the light of a first specific wavelength band is the second IR light N3 having a near infrared wavelength band different from the IR light. The light of a second specific wavelength band is the UV light U2 having a wavelength band shorter than that of the visible light V3. The video signal processing unit 17F combines the IR video signal (for example, the first IR video signal N2VD), the visible video signal V3VD, the second IR video signal N3VD based on the second IR light N3, and the UV video signal U2VD based on the UV light U2. Accordingly, the four-plate camera (for example, the four-plate camera 1F) superimposes the first IR video signal N2VD and the second IR video signal N3VD that are based on imaging of a plurality of beams of IR light having different wavelength bands to be imaged, and thus can display an IR video signal showing a more precise condition of the affected part by reaction (light emission) of the fluorescent reagent on the monitor MN1 together with a color video of a surgical field and a UV video signal showing a condition of the affected part obtained by imaging of UV light, and can appropriately support a medical practice of a user such as a doctor.

In addition, the light of a first specific wavelength band is the second visible light V2 having the same wavelength band as the visible light. The light of a second specific wavelength band is the UV light U2 having a wavelength band shorter than that of the visible light (for example, the first visible light V1). The video signal processing unit 17E combines the visible video signal (for example, the first visible video signal V1VD) and the second visible video signal V2VD that is based on the second visible light V2 to generate the wide dynamic range video signal VVDE, and combines the wide dynamic range video signal VVDE, the IR video signal N1VD, and the UV video signal U2VD that is based on the UV light U2. Accordingly, the four-plate camera (for example, the three-plate camera 1E) superimposes the UV video signal U1VD, the first visible video signal V1VD, the second visible video signal V2VD, and the IR video signal N1VD that are based on imaging of a plurality of beams of light having different wavelength bands imaged by the image sensors of four channels, and thus can display on the monitor MN1 not only the color video having a wide dynamic range of a surgical field and the IR video signal showing a condition of the affected part based on reaction (light emission) of the fluorescent reagent, but also the UV video signal showing a condition of the affected part obtained by imaging of the UV light, and can appropriately support a medical practice for a user such as a doctor.

In addition, the light of a first specific wavelength band is the second visible light V2 having the same wavelength band as the visible light (for example, the first visible light V1). The light of a second specific wavelength band is the second IR light N3 having a near infrared wavelength band different from the IR light (for example, the first IR light N2). The video signal processing unit 17G combines the visible video signal (for example, the first visible video signal V1VD) and the second visible video signal V2VD that is based on the second visible light V2 to generate the wide dynamic range video signal VVDD, and combines the wide dynamic range video signal VVDD, the IR video signal (for example, the first IR video signal N2VD), and the second IR video signal N3VD that is based on the second IR light N3. Accordingly, the four-plate type camera (for example, the four-plate camera 1G) can superimpose the first IR video signal N2VD and the second IR video signal N3VD that are based on imaging of a plurality of beams of IR light having different wavelength bands to be imaged, and further superimpose the first visible video signal V1VD and the second visible video signal V2VD to generate a color video having a wide dynamic range, and thus can display on the monitor MN1 a color video having a wide dynamic range of a surgical field and the IR video signal showing a more precise condition of the affected part by reaction (light emission) of a fluorescent reagent and can support a medical practice for a user such as a doctor.

In addition, the four-plate camera according to the second embodiment includes a first visible prism that causes a first visible image sensor to receive incident first visible light of light from an observation part, a second visible prism that causes a second visible image sensor to receive incident second visible light of the light from the observation part, a first specific prism that causes a first specific image sensor to receive incident light of a first specific wavelength band of the light from the observation part, and a second specific prism that causes a second specific image sensor to receive incident light of a second specific wavelength band of the light from the observation part. The fourth-plate camera includes a video signal processing unit that generates a first visible video signal, a second visible video signal, a first specific video signal, and a second specific video signal of the observation part based on respective imaging outputs of the first visible image sensor, the second visible image sensor, the first specific image sensor, and the second specific image sensor, combines the first visible video signal, the second visible video signal, the first specific video signal, and the second specific video signal, and outputs a combined signal to the monitor MN1.

Accordingly, by superimposing a plurality of beams of visible light having different light amounts (brightness) at the time of surgery or examination, the four-plate camera not only can display the wide dynamic range video signal VVDD having a wider dynamic range than a single color video on the monitor MN1, but also can display a captured video based on two more channels of imaging light. Therefore, the four-plate camera can present, to a user such as a doctor, a video that allows identification of a clear situation of a surgical field by darkly or brightly projecting the surgical field, and can appropriately support a medical practice for the user.

In addition, the light of a first specific wavelength band is the third visible light V4 having the same wavelength band as the first visible light V1. The light of a second specific wavelength band light is the IR light N1 having a wavelength band longer than that of the first visible light V1. The video signal processing unit 17H combines the first visible video signal V1VD, the second visible video signal V2VD, and the third visible video signal V4VD that is based on the third visible light V4 to generate the wide dynamic range video signal VVDH, and combines the wide dynamic range video signal VVDH and the IR video signal N1VD that is based on the IR light N1. Accordingly, since the four-plate camera superimposes the visible video signals of three channels having different light amounts, it is possible to display on the monitor MN1 a video having a wider dynamic range as compared with a single color video. Thus it is possible to present, to a user such as a doctor, a video that makes it easy to understand a more clear and detailed surgical field, and it is possible to appropriately support a medical practice for the user.

In addition, each of the first visible prism and the second visible prism is disposed farther from the observation part side than the first specific prism and the second specific prism. Accordingly, the reflecting film (for example, the third reflecting film FLM5) disposed in the vicinity of a bonding surface between the first visible prism and the second visible prism may be configured to have a characteristic for reflecting visible light having the same wavelength band as visible light incident on the first visible prism, and thus manufacturing accuracy of the reflecting film can be improved as compared with a case where the reflecting film has a characteristic for reflecting IR light having a wavelength band different from the visible light.

Although various embodiments have been described above with reference to the drawings, it is needless to say that the present disclosure is not limited to such examples. It will be apparent to those skilled in the art that various alterations, modifications, substitutions, additions, deletions, and equivalents can be conceived within the scope of the claims, and it should be understood that such changes also belong to the technical scope of the present disclosure. Components in various embodiments described above may be combined freely within a range not deviating from the spirit of the invention.

INDUSTRIAL APPLICABILITY

The present disclosure is useful as a three-plate camera and a four-plate camera that generate and output a clearer fluorescence image of an observation part to which a fluorescent reagent is administered, and support easy understanding of an affected part for a doctor or the like.

What is claimed is:

1. A three-plate camera, comprising:
an IR prism that includes a first incidence surface and a first reflecting film, the first incidence surface being perpendicular to an optical axis direction of light from an observation part, the first incidence surface totally reflecting IR light of the light from the observation part after the first reflecting film reflects the IR light and causing an IR image sensor to receive the IR light of the light from the observation part;
a first visible prism that includes a second incidence surface on which visible light of the light from the observation part which is transmitted through the first reflecting film is incident and a second reflecting film, the second incidence surface totally reflecting a first predetermined percentage of the visible light after the second reflecting film reflects the first predetermined percentage of the visible light and causing a first visible image sensor to receive the first predetermined percentage of the visible light of the light from the observation part, the visible light being transmitted through the IR prism, the first predetermined percentage being in a range of 1% to 30%;

a second visible prism that includes a third incidence surface on which the visible light of the light from the observation part which is transmitted through the second reflecting film is incident and an emission surface, the third incidence surface and the emission surface causing a second visible image sensor to receive a second predetermined percentage of the visible light, of a specific wavelength band, of the light from the observation part, the second predetermined percentage of the visible light being transmitted through the first visible prism, the second predetermined percentage being equal to one-hundred percent minus the first predetermined percentage; and a video signal processor that
generates an IR video signal, a first visible video signal, and a second visible video signal of the observation part based on respective imaging outputs of the IR image sensor, the first visible image sensor, and the second visible image sensor,
combines the IR video signal, the first visible video signal, and the second visible video signal to generate a combined video signal, and
outputs the combined video signal to a monitor,
wherein the video signal processor generates a first exposure control signal for determining a first exposure time of the first visible image sensor, outputs the first exposure control signal to the first visible image sensor, and the first visible image sensor controls the first exposure time of the first visible image sensor based on the first exposure control signal,
wherein the video signal processor generates a second exposure control signal for determining a second exposure time of the second visible image sensor, outputs the second exposure control signal to the second visible image sensor, and the second visible image sensor controls the second exposure time of the second visible image sensor based on the second exposure control signal,
wherein, in response to the first visible video signal, which is controlled by the first exposure time, being different in brightness than the second visible video signal, which is controlled by the second exposure time, the video signal processor combines the first visible video signal and the second visible video signal to generate a wide dynamic range video signal, before combining the IR video signal with the wide dynamic range video signal to generate the combined video signal,
wherein, in response to the first visible video signal, which is controlled by the first exposure time, being same in brightness as the second visible video signal, which is controlled by the second exposure time, the video signal processor combines the first visible video signal and the second visible video signal to generate a high-resolution video signal, before combining the IR video signal with the high-resolution video signal to generate the combined video signal,
wherein the video signal processor outputs the first exposure control signal and the second exposure control signal directly to the first visible image sensor and the second visible image sensor, respectively, and wherein the video signal processor generates the IR video signal without transmitting an exposure control signal to the IR image sensor, and combines the IR video signal with one of the wide dynamic range video signal or the high-resolution video signal by superimposition to generate the combined video signal.

2. The three-plate camera according to claim 1, wherein the visible light of the specific wavelength band has a same wavelength band as the visible light.

3. The three-plate camera according to claim 1, wherein the video signal processor combines the first visible video signal and the second visible video signal by superimposition.

4. A camera, comprising:
a first visible prism that includes a first incidence surface and a first reflecting film, the first incidence surface totally reflecting first visible light of light from an observation part after the first reflecting film reflects the first visible light and causing a first visible image sensor to receive the first visible light of light from the observation part;

a second visible prism that includes a second incidence surface and a second reflecting film, the second incidence surface totally reflecting a first predetermined percentage of second visible light of the light from the observation part after the second reflecting film reflects the first predetermined percentage of the second visible light and causing a second visible image sensor to receive the first predetermined percentage of the second visible light of the light from the observation part, the second visible light being transmitted through the first visible prism, the first predetermined percentage being in a range of 1% to 30%;

a specific prism that includes a third incidence surface and an emission surface, the third incidence surface and the emission surface causing a specific image sensor to receive a second predetermined percentage of the second visible light, of a specific wavelength band, of the light from the observation part, the second predetermined percentage of the second visible light being transmitted through the second visible prism, the second predetermined percentage being equal to one-hundred percent minus the first predetermined percentage; and a video signal processor that
generates a first visible video signal, a second visible video signal, and a specific video signal of the observation part based on respective imaging outputs of the first visible image sensor, the second visible image sensor, and the specific image sensor,
combines the first visible video signal, the second visible video signal, and the specific video signal to generate a combined video signal, and
outputs the combined video signal to a monitor,
wherein the video signal processor generates a first exposure control signal for determining a first exposure time of the first visible image sensor, outputs the first exposure control signal to the first visible image sensor, and the first visible image sensor controls the first exposure time of the first visible image sensor based on the first exposure control signal,
wherein the video signal processor generates a second exposure control signal for determining a second exposure time of the second visible image sensor, outputs the second exposure control signal to the second visible image sensor, and the second visible image sensor controls the second exposure time of the second visible image sensor based on the second exposure control signal, wherein, in response to the first visible video signal, which is controlled by the first exposure time, being different in brightness than the second visible video signal, which controls the second exposure time, the video signal processor combines the first visible video signal and the second visible video signal to generate a wide dynamic range video signal, before combining the specific video signal with the wide dynamic range video signal to generate the combined video signal, wherein, in response to the first visible video signal, which is controlled by the first exposure time, being same in brightness as the second visible video signal, which controls the second exposure time, the video signal processor combines the first visible video signal and the second visible video signal to generate a high-resolution video signal, before combining the specific video signal with the high-resolution video signal to generate the combined video signal, wherein the video signal processor outputs the first exposure control signal and the second exposure control signal directly to the first visible image sensor and the second visible image sensor, respectively, and wherein the video signal processor generates the specific video signal without transmitting an exposure control signal to the specific image sensor, and combines the specific video signal with one of the wide dynamic range video signal or the high-resolution video signal by superimposition to generate the combined video signal.

5. The camera according to claim 4, wherein the second visible light of the specific wavelength band has a same wavelength band as the first visible light and the second visible light, and wherein the video signal processor combines the first visible video signal, the second visible video signal, and a third visible video signal that is generated based on the third visible light to generate the wide dynamic range video signal.

6. The camera according to claim 4, wherein each of the second visible prism and the specific prism is disposed farther from an observation part side than the first visible prism.

7. A four-plate camera, comprising:

an IR prism that includes a first incidence surface and a first reflecting film, the first incidence surface being perpendicular to an optical axis direction of light from an observation part, the first incidence surface totally reflecting IR light of the light from the observation part after the first reflecting film reflects the IR light and causing an IR image sensor to receive the IR light of the light from the observation part;

a first visible prism that includes a second incidence surface on which visible light of the light from the observation part which is transmitted through the first reflecting film is incident and a second reflecting film, the second incidence surface totally reflecting a first predetermined percentage of the visible light after the second reflecting film reflects the first predetermined percentage of the visible light and causing a first visible image sensor to receive the first predetermined percentage of the visible light of the light from the observation part, the first predetermined percentage being in a range of 1% to 30%;

a second visible prism that includes a third incidence surface on which the visible light of the light from the observation part which is transmitted through the second reflecting film is incident and a third reflecting film, the third incidence surface totally reflecting a second predetermined percentage of the visible light of a first specific wavelength band after the second reflecting film reflects the second predetermined percentage of the visible light of the first specific wavelength band and causing a second visible image sensor to receive the second predetermined percentage of the visible light, of the first specific wavelength band, of the light from the observation part, the second predetermined percentage of the visible light being transmitted through the first visible prism, the second predetermined percentage being equal to one-hundred percent minus the first predetermined percentage;

a first specific prism that includes a fourth incidence surface on which specific light of the light from the observation part which is transmitted through the third reflecting film is incident and an emission surface, the fourth incidence surface and the emission surface causing a first specific image sensor to receive the specific light, of a second specific wavelength band, of the light from the observation part; and a video signal processor that
  generates an IR video signal, a first visible video signal, a second visible video signal, and a first specific video signal of the observation part based on respective imaging outputs of the IR image sensor, the first visible image sensor, the second visible image sensor, and the first specific image sensor,
  combines the IR video signal, the first visible video signal, the second visible video signal, and the first specific video signal to generate a combined video signal, and
  outputs the combined video signal to a monitor, wherein the video signal processor generates a first exposure control signal for determining a first exposure time of the first visible image sensor, outputs the first exposure control signal to the first visible image sensor, and the first visible image sensor controls the first exposure time of the first visible image sensor based on the first exposure control signal, wherein the video signal processor generates a second exposure control signal for determining a second exposure time of the second visible image sensor, outputs the second exposure control signal to the second visible image sensor, and the second visible image sensor controls the second exposure time of the second visible image sensor based on the second exposure control signal, wherein, in response to the first visible video signal, which is controlled by the first exposure time, being different in brightness than the second visible video signal, which is controlled by the second exposure time, the video signal processor combines the first visible video signal and the second visible video signal to generate a wide dynamic range video signal, before combining the IR video signal and the first specific video signal with the wide dynamic range video signal to generate the combined video signal, wherein, in response to the first visible video signal, which is controlled by the first exposure time, being same in brightness as the second visible video signal, which is controlled by the second exposure time, the video signal processor combines the first visible video signal and the second visible video signal to generate a high-resolution video signal, before combining the IR video signal and the first specific video signal with the high-resolution video signal to generate the combined video signal, wherein the video signal processor outputs the first exposure control signal and the second exposure control signal directly to the first visible image sensor and the second visible image sensor, respectively, and wherein the video signal processor generates the IR video signal and the first specific video signal without transmitting exposure control signals to the IR image sensor and the first specific image sensor, and combines the IR video signal and the first specific video signal with one of the wide dynamic range video signal or the high-resolution video signal by superimposition to generate the combined video signal.

8. The four-plate camera according to claim 7,
wherein the specific light of the second specific wavelength band is UV light having a wavelength band shorter than that of the visible light, and
wherein the video signal processor combines the IR video signal, the first visible video signal, the second visible video signal, and a UV video signal generated based on the UV light to generate the combined video signal.

9. The four-plate camera according to claim 7,
wherein the second predetermined percentage of the visible light of the first specific wavelength band has a same wavelength band as the first predetermined percentage of the visible light,
wherein the specific light of the second specific wavelength band is UV light having a wavelength band shorter than that of the first predetermined percentage of the visible light, and
wherein, in response to the first visible video signal being different in brightness than the second visible video signal, the video signal processor combines the first visible video signal and the second visible video signal to generate the wide dynamic range video signal, and combines the wide dynamic range video signal, the IR video signal, and a UV video signal that is generated based on the UV light to generate the combined video signal.

10. The four-plate camera according to claim 7,
wherein the visible light of the first specific wavelength band has a same wavelength band as the visible light,
wherein the specific light of the second specific wavelength band is second IR light having a near-infrared wavelength band different from that of the IR light, and
wherein, in response to the first visible video signal being different in brightness than the second visible video signal, the video signal processor combines the first visible video signal and the second visible video signal to generate the wide dynamic range video signal, and combines the wide dynamic range video signal, the IR video signal, and a second IR video signal that is generated based on the second IR light to generate the combined video signal.

11. A four-plate camera, comprising:
a first visible prism that includes a first incidence surface and a first reflecting film, the first incidence surface totally reflecting a first predetermined percentage of visible light of light from an observation part after the first reflecting film reflects the first predetermined percentage of the visible light and causing a first visible image sensor to receive the first predetermined percentage of the visible light of the light from the observation part, the first predetermined percentage being in a range of 1% to 30%;

a second visible prism that includes a second incidence surface and a second reflecting film, the second incidence surface totally reflecting a second predetermined percentage of the visible light of the light from the observation part after the second reflecting film reflects the second predetermined percentage of the visible light and causing a second visible image sensor to receive a second predetermined percentage of the visible light of the light from the observation part, the second predetermined percentage of the visible light being transmitted through the first visible prism, the second predetermined percentage being equal to one-hundred percent minus the first predetermined percentage;

a first specific prism that includes a third incidence surface and a first emission surface, the third incidence surface and the first emission surface causing a first specific image sensor to receive first specific light of a first specific wavelength band of the light from the observation part;

a second specific prism that includes a fourth incidence surface and a second emission surface, the fourth incidence surface and the fourth emission surface causing a second specific image sensor to receive second specific light of a second specific wavelength band of the light from the observation part; and a video signal processor that
generates a first visible video signal, a second visible video signal, a first specific video signal, and a second specific video signal of the observation part based on respective imaging outputs of the first visible image sensor, the second visible image sensor, the first specific image sensor, and the second specific image sensor,
combines the first visible video signal, the second visible video signal, the first specific video signal, and the second specific video signal to generate a combined video signal, and
outputs the combined video signal to a monitor, wherein the video signal processor generates a first exposure control signal for determining a first exposure time of the first visible image sensor, outputs the first exposure control signal to the first visible image sensor, and the first visible image sensor controls the first exposure time of the first visible image sensor based on the first exposure control signal, wherein the video signal processor generates a second exposure control signal for determining a second exposure time of the second visible image sensor, outputs the second exposure control signal to the second visible image sensor, and the second visible image sensor controls the second exposure time of the second visible image sensor based on the second exposure control signal, wherein, in response to the first visible video signal, which is controlled by the first exposure time, being different in brightness than the second visible video signal, which is controlled by the second exposure time, the video signal processor combines the first visible video signal and the second visible video signal to generate a wide dynamic range video signal, before combining at least the second specific video signal with the wide dynamic range video signal to generate the combined video signal, wherein, in response to the first visible video signal, which controls the first exposure time, being same in brightness as the second visible video signal, which controls the second exposure time, the video signal processor combines the first visible video signal and the second visible video signal to generate a high-resolution video signal, before combining at least the second specific video signal with the high-resolution video signal to generate the combined video signal, wherein the video signal processor outputs the first exposure control signal and the second exposure control signal directly to the first visible image sensor and the second visible image sensor, respectively, and wherein the video signal processor generates at least the second specific video signal without transmitting an exposure control signal to the second specific image sensor, and combines at least the second specific video signal with one of the wide dynamic range video signal or the high-resolution video signal by superimposition to generate the combined video signal.

12. The four-plate camera according to claim 11, wherein the first specific light of the first specific wavelength band has a same wavelength band as the first predetermined percentage of the visible light, wherein the second specific light of the second specific wavelength band is IR light having a wavelength band longer than that of the first predetermined percentage of the visible light, and wherein, in response to the first visible video signal being different in brightness than the second visible video signal, the video signal processor combines the first visible video signal, the second visible video signal, and a third visible video signal that is generated based on the second visible light to generate the wide dynamic range video signal, and combines the wide dynamic range video signal and an IR video signal generated based on the IR light to generate the combined video signal.

13. The four-plate camera according to claim 11, wherein each of the first visible prism and the second visible prism is disposed farther from an observation part side than the first specific prism and the second specific prism.

* * * * *